United States Patent
Nakazawa et al.

(10) Patent No.: US 10,628,948 B2
(45) Date of Patent: Apr. 21, 2020

(54) IMAGE REGISTRATION DEVICE, IMAGE REGISTRATION METHOD, AND IMAGE REGISTRATION PROGRAM

(71) Applicant: JAPAN SCIENCE AND TECHNOLOGY AGENCY, Kawaguchi-shi, Saitama (JP)

(72) Inventors: Atsushi Nakazawa, Kyoto (JP); Christian Nitschke, Reutlingen (DE)

(73) Assignee: Japan Science and Technology Agency, Kawaguchi-shi (JP)

( * ) Notice: Subject to any disclaimer, the term of this patent is extended or adjusted under 35 U.S.C. 154(b) by 167 days.

(21) Appl. No.: 15/413,629

(22) Filed: Jan. 24, 2017

(65) Prior Publication Data

US 2017/0169578 A1  Jun. 15, 2017

Related U.S. Application Data

(63) Continuation of application No. PCT/JP2015/071027, filed on Jul. 23, 2015.

(30) Foreign Application Priority Data

Jul. 24, 2014 (JP) .................... 2014-150848

(51) Int. Cl.
*H04N 13/344* (2018.01)
*H04N 13/383* (2018.01)
(Continued)

(52) U.S. Cl.
CPC ............ *G06T 7/337* (2017.01); *A61B 3/0025* (2013.01); *A61B 3/113* (2013.01); *A61B 3/14* (2013.01);
(Continued)

(58) Field of Classification Search
CPC ........ G06F 3/0304; G06F 21/32; G06F 3/011; G06F 2203/011; G06F 3/00; G06F 3/012;
(Continued)

(56) References Cited

U.S. PATENT DOCUMENTS 6,389,179 B1   5/2002  Katayama et al.
8,077,914 B1   12/2011  Kaplan
(Continued)

FOREIGN PATENT DOCUMENTS

EP   2 826 414 A1   1/2015
JP   H09-322040 A   12/1997
(Continued)

OTHER PUBLICATIONS

Christian Nitschke et al., "Corneal Imaging Revisited: An Overview of Corneal Reflection Analysis and Applications," IPSJ Trans. Computer Vision and Applications, vol. 5, pp. 1-18, Jan. 2013. Retrieved from the Internet: URL: https://www.jstage.jst.go.jp/article/ipsjtcva/5/0/5_1/_pdf/-char/en.
(Continued)

*Primary Examiner* — Dave Czekaj
*Assistant Examiner* — Samuel D Fereja
(74) *Attorney, Agent, or Firm* — Amster, Rothstein & Ebenstein LLP

(57) ABSTRACT

An image registration device includes a mapping section for deciding a first mapping for transforming the first image to an environmental map and a second mapping for transforming the second image to an environmental map, a corresponding point pair extractor for extracting a pair of corresponding points by detecting one point in the first image and the corresponding one point in the second image, a rotational mapping deriver for deriving a rotational mapping for registering an image of the first image in the environmental map and an image of the second image in the environmental map
(Continued)

with each other, based on positions and local feature amounts of the points in the first and second images, and a registration section for registering the data of the first image with the data of the second image based on the first mapping, the rotational mapping, and the second mapping.

7 Claims, 17 Drawing Sheets

(51) Int. Cl.
  G06T 7/33      (2017.01)
  A61B 3/113     (2006.01)
  G06T 7/60      (2017.01)
  G06T 5/50      (2006.01)
  G06T 7/00      (2017.01)
  H04N 5/225     (2006.01)
  A61B 3/00      (2006.01)
  A61B 3/14      (2006.01)
  H04N 7/18      (2006.01)
  G06K 9/00      (2006.01)

(52) U.S. Cl.
  CPC ............... *G06T 5/50* (2013.01); *G06T 7/00* (2013.01); *G06T 7/60* (2013.01); *H04N 5/225* (2013.01); *H04N 7/181* (2013.01); *G06K 9/00604* (2013.01); *G06T 2207/30201* (2013.01)

(58) Field of Classification Search
  CPC .... G06F 3/017; G06F 3/04817; G06F 3/0482; G06F 17/145; G06F 21/316; G06F 21/64; G06F 3/005; G06F 3/038; G06F 3/044; G06F 1/163; G06F 3/01; G06F 3/0346; G06F 9/451; G06K 9/00597; G06K 9/00335; G06K 9/00248; G06K 9/00617; G06K 9/00899; G06K 9/00906; G06K 9/52; G06K 9/46; G06K 9/00281; G06K 9/4671; G06K 9/481; G06K 9/00261; G06K 9/00268; G06K 9/00912; G06K 9/00986; G06K 9/3233; G06K 9/4633; G06K 9/00845; G06K 9/4642; G06K 9/6256; G06K 9/00604; G06K 9/0061; G06K 9/00; G06K 9/4661; G06K 2009/4666; G06K 9/00255; G06K 9/3216; G06K 9/033; G06K 9/78; A61B 3/113; A61B 3/0025; A61B 3/14; A61B 3/107; A61B 5/0071; A61B 5/11; A61B 5/18; A61B 5/6814; A61B 3/152; A61B 3/15; A61B 5/117; A61B 2562/0219; A61B 2562/0223; A61B 3/0041; A61B 3/032; A61B 3/111; A61B 3/18; A61B 5/7257; G06T 2207/10012; G06T 2207/10016; G06T 7/70; G06T 7/20; G06T 7/337; G06T 7/77; G06T 11/20; G06T 2207/30201; G06T 7/73; G06T 19/006; G06T 2207/20076; G06T 2207/30041; G06T 2207/30196; G06T 3/4038; G06T 2207/10004; G06T 2207/20008; G06T 2207/20061; G06T 3/40

See application file for complete search history.

(56) References Cited

U.S. PATENT DOCUMENTS

| | | | |
|---|---|---|---|
| 2002/0126890 A1* | 9/2002 | Katayama | ............. G06T 3/4038 382/154 |
| 2005/0063608 A1 | 3/2005 | Clarke et al. | |
| 2007/0047775 A1* | 3/2007 | Okubo | ............... G06K 9/00248 382/118 |
| 2013/0295994 A1* | 11/2013 | Guitteaud | .............. F16M 13/00 455/556.1 |
| 2015/0070470 A1* | 3/2015 | McMurrough | ......... G06F 3/013 348/46 |
| 2015/0154758 A1 | 6/2015 | Nakazawa et al. | |

FOREIGN PATENT DOCUMENTS

| | | |
|---|---|---|
| JP | 2001-108933 A | 4/2001 |
| JP | 2005-100407 A | 4/2005 |
| JP | 2009-253786 A | 10/2009 |
| JP | 2010-056661 A | 3/2010 |
| JP | 2010-072188 A | 4/2010 |
| JP | 2010-102215 A | 5/2010 |
| JP | 2014-109841 A | 6/2014 |
| WO | 2014/021169 A1 | 2/2014 |

OTHER PUBLICATIONS

European Patent Office, "Extended European Search Report," issued in European Patent Application No. 15 825 115.7, which is a European Counterpart of U.S. Appl. No. 15/413,629, dated Feb. 5, 2018, 9 pages.

Written Opinion (English translation) relating to International Application No. PCT/JP2015/071027, dated Feb. 2, 2017.

Atsushi Nakazawa and Christian Nitschke, "Point of Gaze Estimation through Corneal Surface Reflection in an Active Illumination Environment," 12th European Conference on Computer Vision ECCV 2012, Oct. 7-13, 2012, pp. 159-172.

Korean Intellectual Property Office, "Office Action," issued in Korean Patent Application No. 10-2017-7000056, which is a Korean counterpart of U.S. Appl. No. 15/413,629, dated Nov. 21, 2017, 13 pages (6 pages of English Translation of Office Action and 7 pages of Office Action).

International Search Report received for PCT Patent Application No. PCT/JP2015/071027, dated Sep. 1, 2015, 4 pages (2 pages of English Translation and 2 pages of PCT search report).

Christian Nitschke and Atsushi Nakazawa, "Super resolution scene reconstruction using corneal reflections," The Institute of Electronics, Information and Communication Engineers, Technical Report of IEICE, PRMU 2012-63 (Oct. 2012), pp. 65-70.

Anonymous ECCV submission, "Registration of eye reflection and scene images using random resample consensus," ECCV-14 submission ID 876, pp. 1-15.

\* cited by examiner

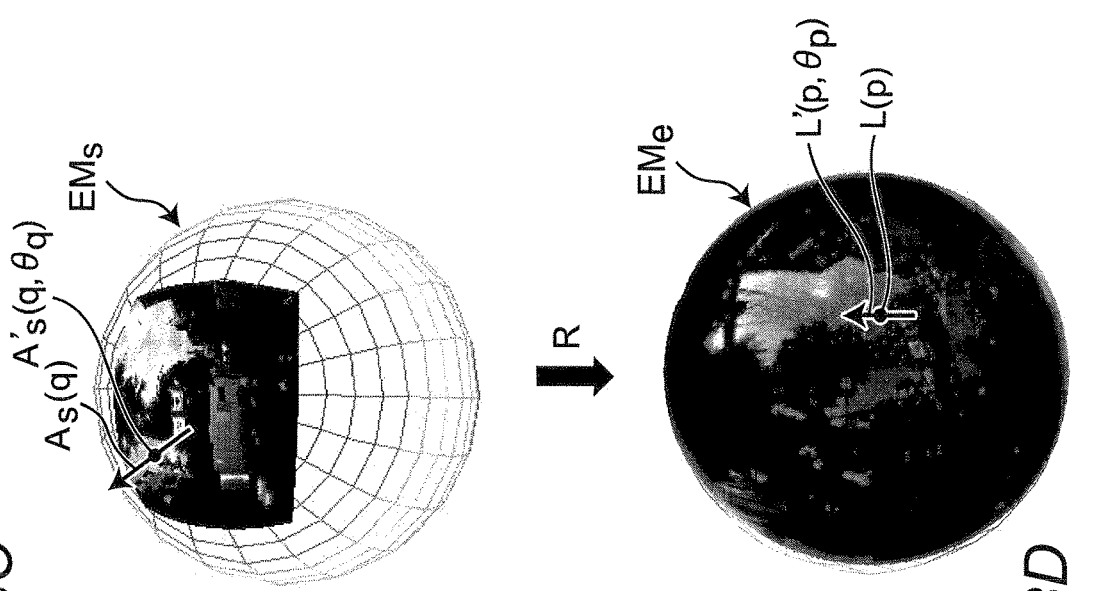
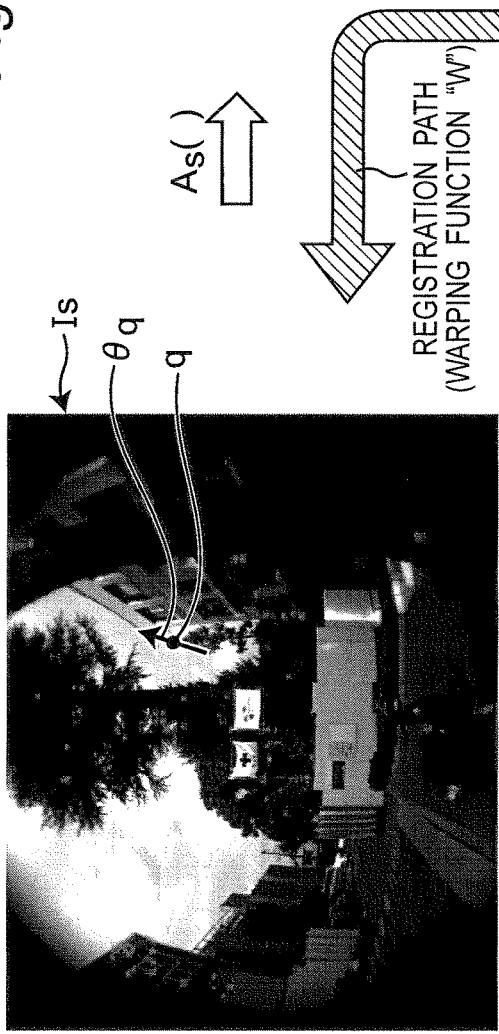
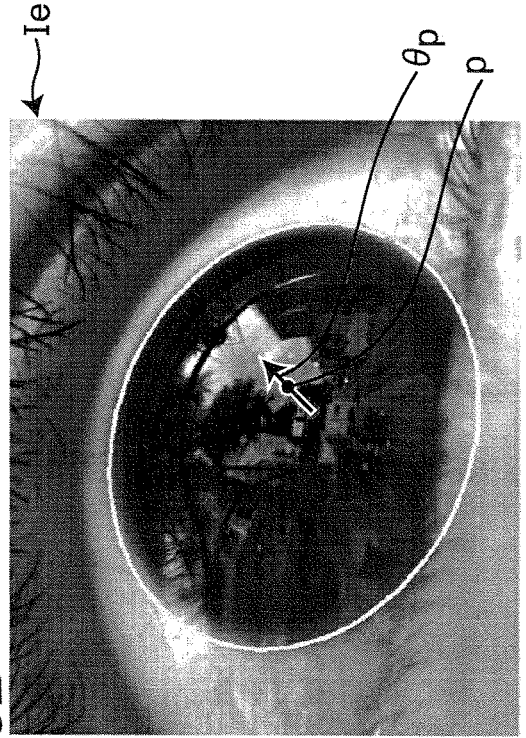
Fig.3A  Fig.3B  Fig.3C  Fig.3D

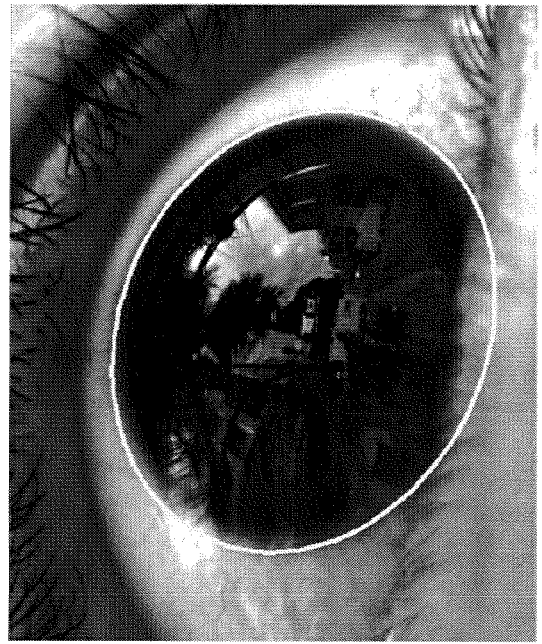
*Fig.6B*  Ie'
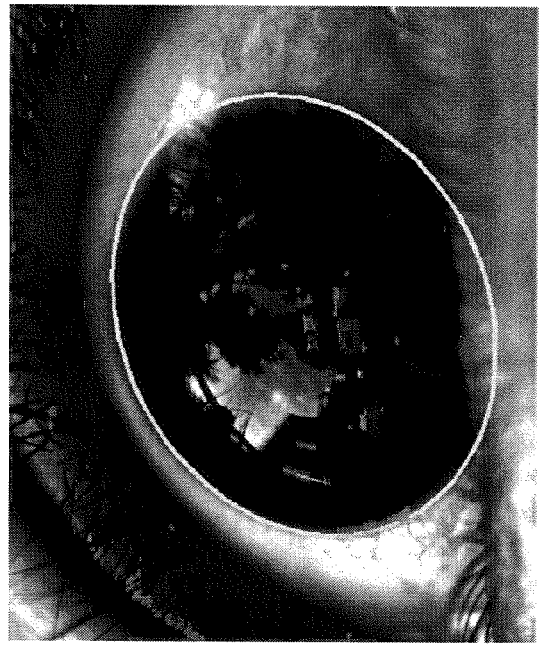
*Fig.6C*  Ie
*Fig.6A*  Is

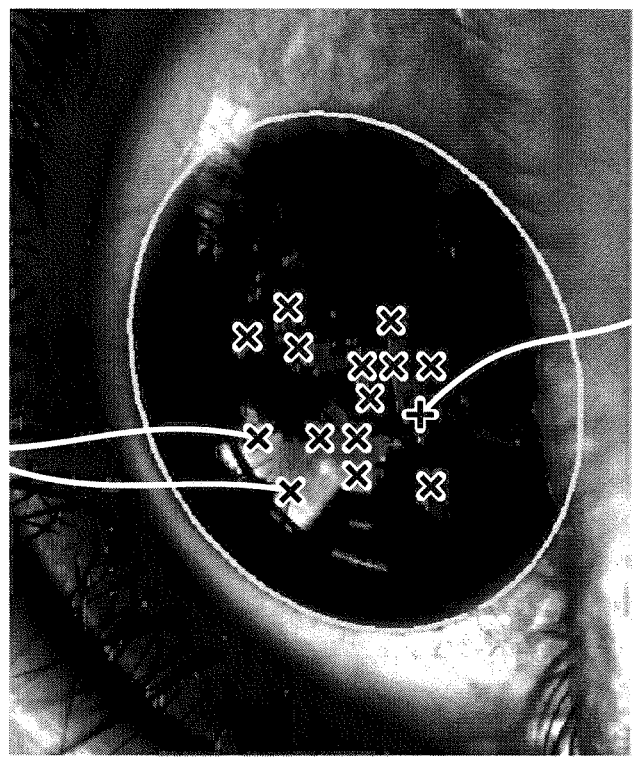
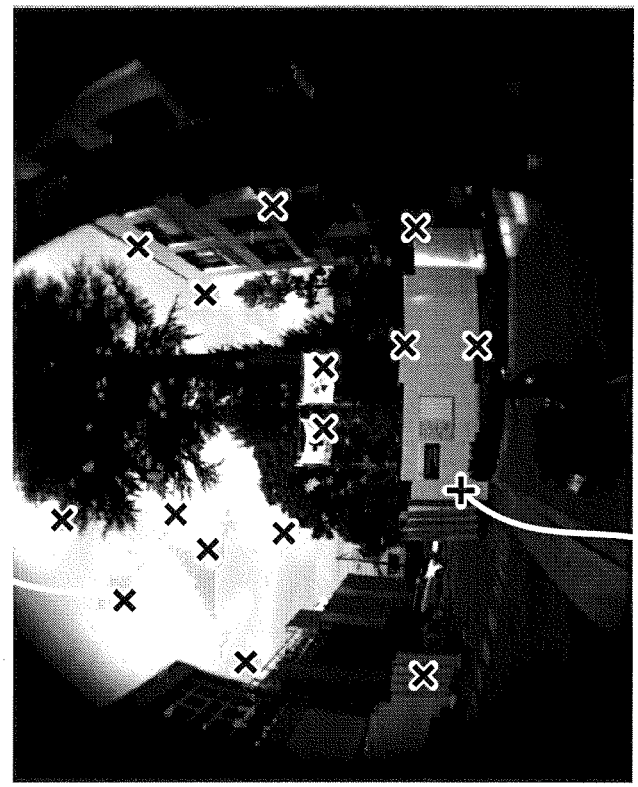
Fig. 13

Fig. 15
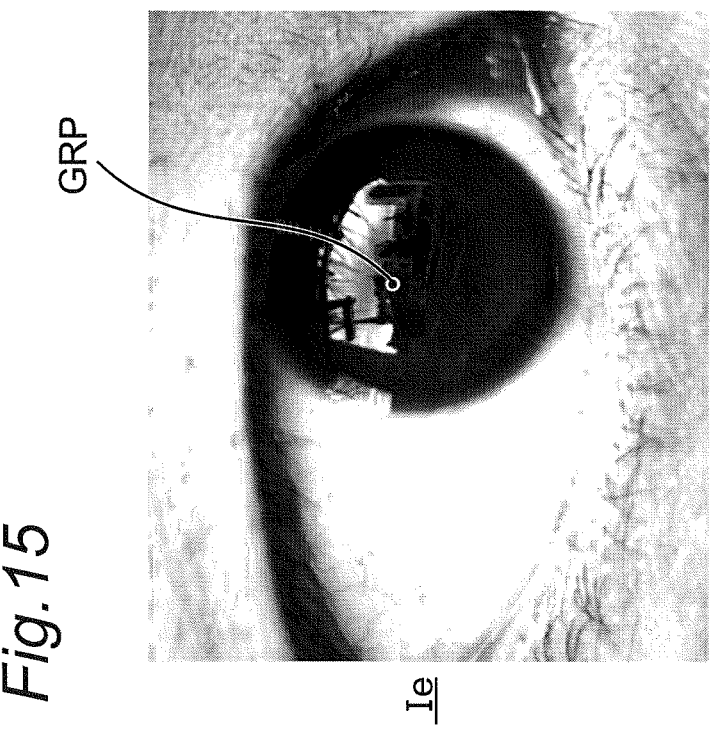

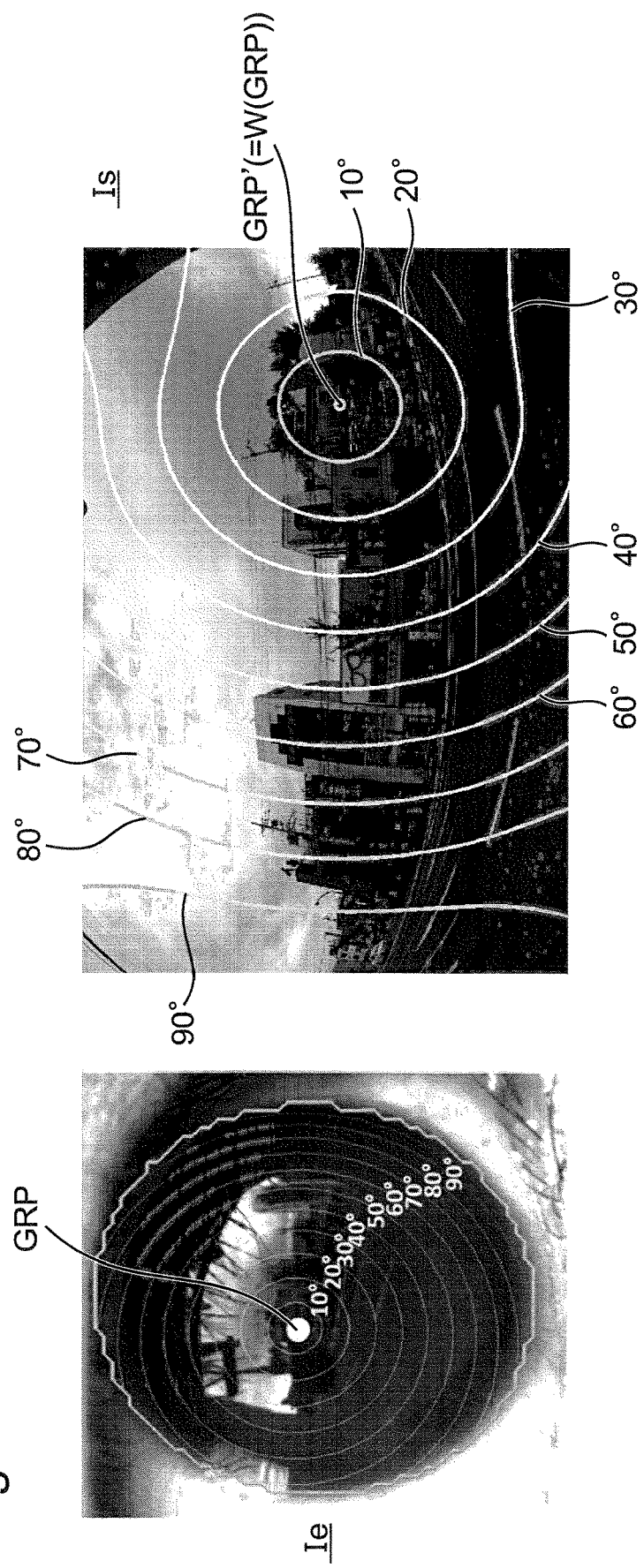

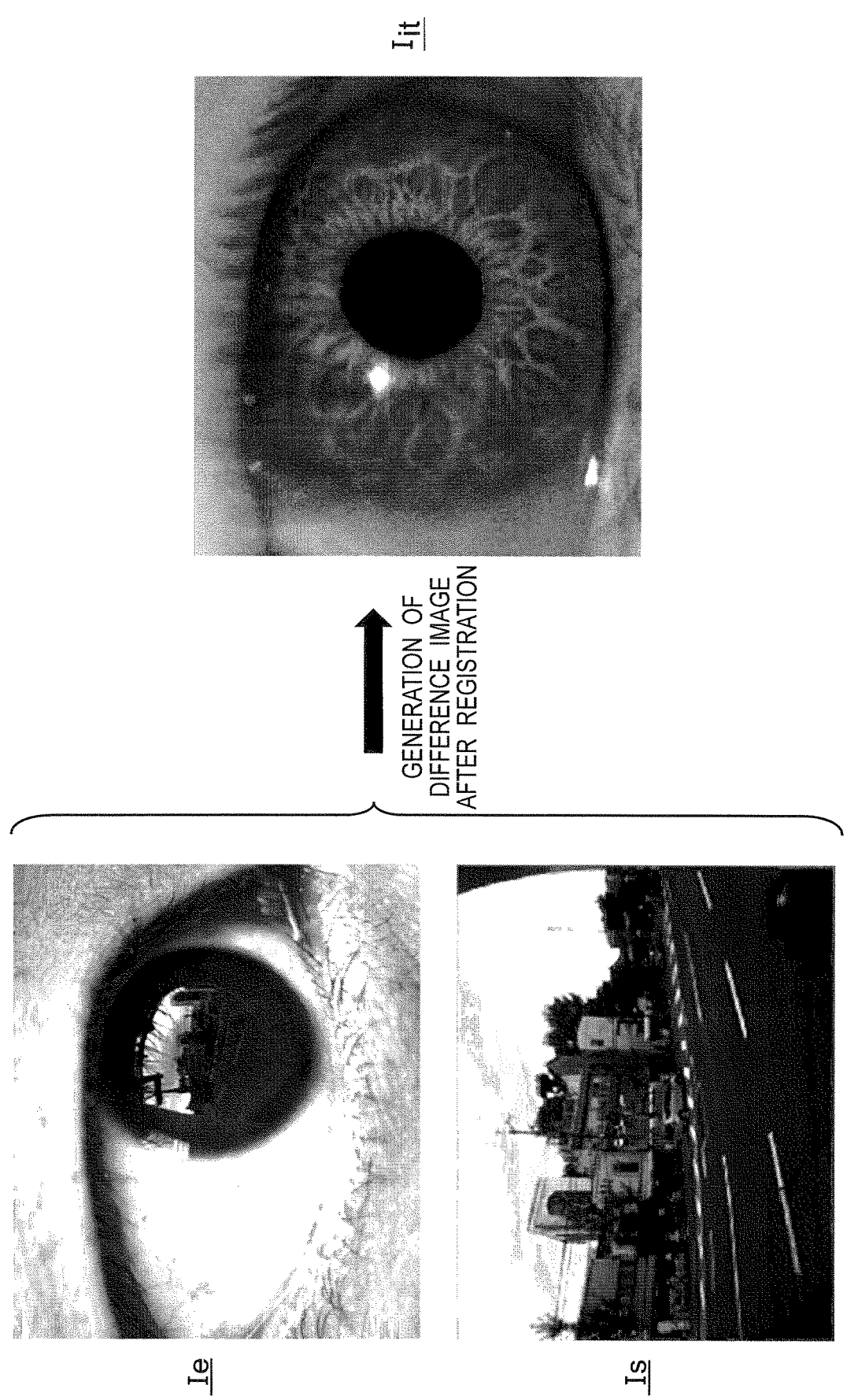

IMAGE REGISTRATION DEVICE, IMAGE REGISTRATION METHOD, AND IMAGE REGISTRATION PROGRAM

TECHNICAL FIELD

The present invention relates to a device for image registration or image alignment.

BACKGROUND ART

The patent document 1 describes a device that estimates a point (gazing point) gazed by a subject (or target person) and a personal parameter of the subject. The device obtains an image (eye image) including an image of an eyeball of the subject, estimates an eyeball attitude (that is, a direction of an optical axis of the eyeball), and estimates a direction (gazing direction) of a visual line of the subject from the eye image. The device quantifies a deviation amount between the optical axis direction of the eyeball and the visual line direction as a personal parameter.

CITATION LIST

Patent Literature

Patent document 1: International Patent Publication No. WO2014/021169

SUMMARY OF THE INVENTION

Generally an image (eye image) obtained by capturing an image of the eyeball includes an image (a corneal-surface reflection image) of light specularly reflected from a cornea of the eyeball. The corneal-surface reflection image corresponds to a sight actually seen by the subject. The corneal-surface reflection image corresponds to the sight actually seen by the subject. Based on the fact, nowadays, attempts to restore the sight seen by the subject are actively made using the image (scene image) of a scene surrounding the subject and the eye image including the corneal-surface reflection image. In various applications derived from such a kind of investigations and results therefrom, the registration between the eye image and the scene image obtained by capturing an image of the scene surrounding the subject different from the eye image are an important technology.

However, the corneal-surface reflection image includes many noise components, and thus it is very difficult to perform the registration or alignment between the eye image and the scene image in a robust manner.

The present invention provides a device that can robustly perform image registration (or image alignment) between at least two images such as the eye image and the scene image.

In one aspect of the present invention, an image registration device is provided. The image registration device includes: an obtaining section configured to obtain data of a first image and data of a second image; a storage device configured to store the data of the first image and the data of the second image; a mapping section configured to decide a first mapping for transforming the first image to an environmental map, and a second mapping for transforming the second image to an environmental map; a corresponding point pair extractor configured to extract a pair of corresponding points by detecting one point in the first image and one point in the second image which corresponds to the one point in the first image; a rotational mapping deriver configured to derive a rotational mapping for registering an image of the first image in the environmental map and an image of the second image in the environmental map with each other, based on positions and local feature amounts of the one point in the first image and the one point in the second image which compose the pair of corresponding points; and a registration section configured to register the data of the first image stored in the storage device with the data of the second image stored in the storage device in order to generate data of the first image registered with the second image, based on the first mapping, the rotational mapping, and the second mapping.

The image registration device according to one aspect of the present invention can robustly perform image registration (or image alignment) between at least two images.

BRIEF DESCRIPTION OF DRAWINGS

FIGS. 3A to 3D are schematic diagrams illustrating an image registration method according to an embodiment.

FIGS. 6A to 6C are views illustrating examples of the obtained eye image, the obtained scene image, and the mirror-reversed eye image, respectively.

FIG. 13 is a view illustrating an example in which secondary corresponding points on the scene image, which correspond to the secondary corresponding points randomly plotted on the eye image, are plotted based on a warping function derived according to a correspondence in the i-th initial corresponding point pair.

FIG. 15 is a view illustrating an application example (viewpoint estimation) of the image registration device of the embodiment.

FIG. 16 is a view illustrating an application example (peripheral visual field estimation) of the image registration device of the embodiment.

FIG. 17 is a view illustrating an application example (generation of an iris recognition image) of the image registration device of the embodiment.

MODE FOR CARRYING OUT THE INVENTION

1. Background Leading to the Present Invention

Figure 1:
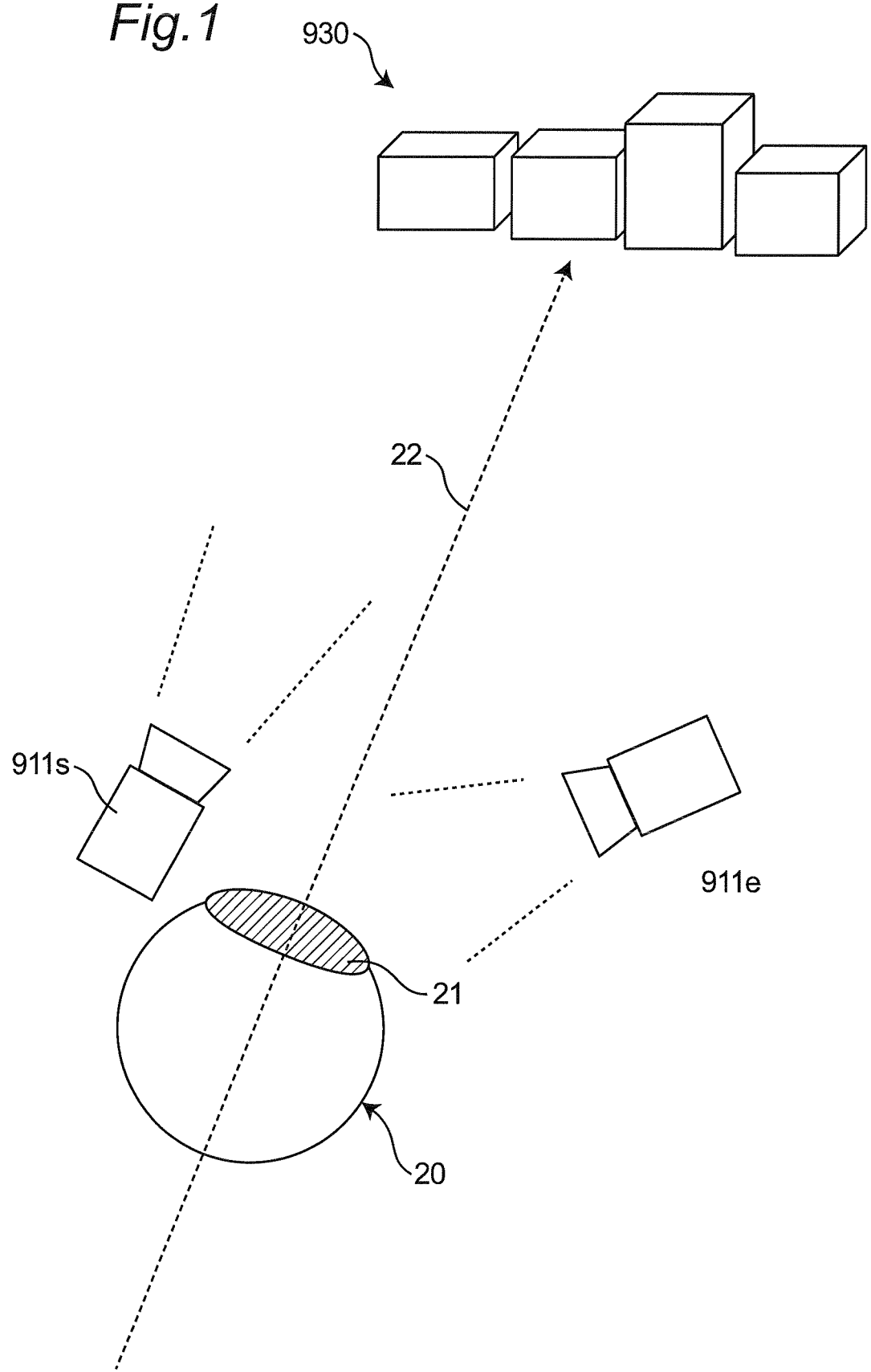
FIG. 1 is a view illustrating a disposition example of an eye camera and a scene camera.

Background leading to the present invention will be described by taking a system as shown in FIG. 1 as an example. The system shown in FIG. 1 includes an eye camera 911e that mainly captures an image of eyeball 20 (mainly a cornea 21) of a subject and a scene camera 911s that captures an image of a sight (scene) seen by the subject. The scene camera 911s is installed such that an imaging direction is substantially aligned with a visual line direction of the subject. The system also includes a computer (not illustrated). The computer estimates the visual line direction of the subject from an image (eye image) captured by the eye camera 911e, and tries to finely restore the sight seen by the subject using the image (scene image) captured by the scene camera 911s.

Figure 2A:
FIG. 2A is a view illustrating an example of an eye image captured with an eye camera.
Figure 2B:
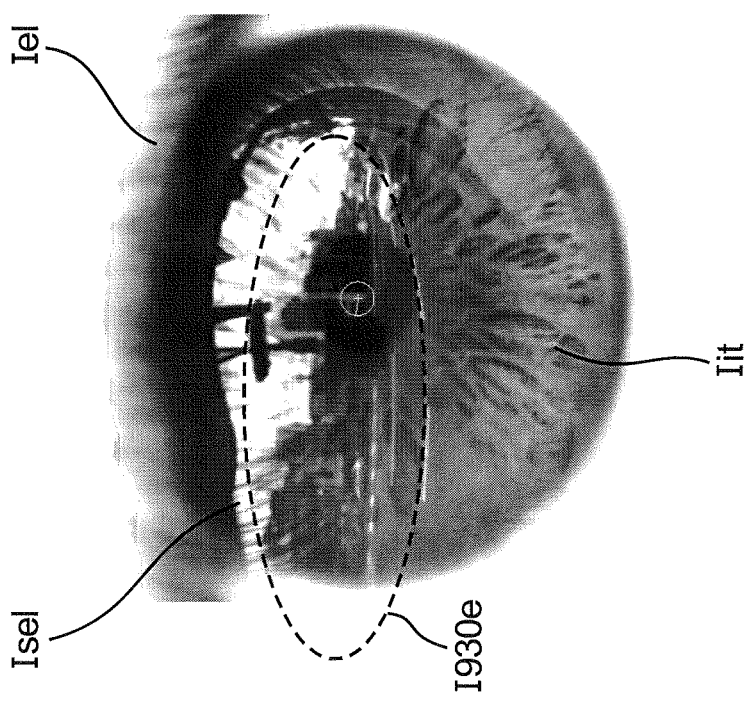
FIG. 2B is a view illustrating an example of a scene image captured with a scene camera.

FIGS. 2A and 2B are views illustrating examples of the eye image and the scene image, which are captured by the eye camera 911e and the scene camera 911s of the system shown in FIG. 1, respectively. FIG. 2A illustrates an example of an image (eye image) Ie9 of the subject's eyeball captured by the eye camera 911e. FIG. 2B illustrates an example of an image (scene image) Is9 of the sight (scene), which is seen by the subject and captured with the scene camera 911s.

The computer estimates the sight (scene) seen by the subject from an image of the reflection light from the corneal surface (for example, seen in a region 1930e). The computer obtains an image corresponding to the scene from, for example, a region 1930s of a scene image Is9, and restores the sight seen by the subject using the fine scene image Is9 based on the obtained image.

However, referring to the eye image Ie9, the corneal-surface reflection image has a relatively low contrast, and is full of noises such as an iris texture Iit, an eyelash Iel, and an eyelash shadow Isel. Further, the cornea has a curved surface, and thus the image of the scene reflected in the cornea is subjected to a nonlinear deformation. Therefore, with the conventional image registration (or image alignment) technique, it is difficult to perform robustly the image registration between the eye image Ie9 and the scene image Is9.

2. Outline of Embodiment of Present Invention

The inventors propose the following new image registration device and method. An outline of an image registration method performed by an image registration device according to an embodiment of the present invention will be described below with reference to FIGS. 3A to 3D.

The image registration device of the embodiment obtains data of an eye image Ie and a scene image Is, and stores the data in a storage device such as a memory. The image registration device decides mapping (first mapping and second mapping) which transforms each of the scene image Is and the eye image Ie to an environmental map (EM). As used herein, "the environmental map" means a map associated with a ray environment surrounding an image capturing means, and the environmental map is generated when light incident on the center of the image capturing means is mapped on a spherical surface having a predetermined radius. FIG. 3C illustrates an example of an environmental map EMs for the scene image Is. The scene image on the environmental map EMs is illustrated in FIG. 3C. FIG. 3D illustrates an example of an environmental map EMe for the eye image Ie, and the eye image on the environmental map EMe is illustrated in FIG. 3D. In this case, it is assumed that As( ) is mapping (transform function) for transferring (transforming) the scene image Is to the environmental map EMs, and that L( ) is mapping (function) for transferring (transforming) the corneal-surface reflection image of the eye image Ie to the environmental map EMe. For example, a pixel $x_1$ of the scene image Is is transferred to $As(x_1)$ on the environmental map EMs through the mapping As, and a pixel $x_2$ of the eye image Ie is transferred to $L(x_2)$ on the environmental map EMe through the mapping L.

Then, the image registration device obtains at least one pair (hereinafter, also referred to as an initial corresponding point pair) of feature points which correspond to each other (for example, a pair of a point p and a point q) between the scene image Is (first image) and (the corneal-surface reflection image of) the eye image Ie (second image). The image registration device can use known techniques (such as SIFT (Scale-Invariant Feature Transform) and SURF (Speeded Up Robust Features)) in order to detect the corresponding point. According to the known techniques for detecting the feature points such as SIFT and SURF, direction (orientation) information ($\theta_p$ and $\theta_q$) can be calculated as a local feature amount with respect to the respective feature points (the point p and the point q) of the detected corresponding point pair. Using the orientation information ($\theta_p$ and $\theta_q$) and positional information about the corresponding points (feature points) (the point p and the point q), the image registration device decides rotational mapping R for registering and aligning the scene image on the environmental map EMs with the corneal-surface reflection image on the environmental map EMe. In this case, it is assumed that the environmental map EMs and the environmental map EMe are substantially equal to each other, and therefore it is assumed that the image registration (or alignment) can be represented by rotational mapping R (for example, a pixel $q_1$ of the scene image Is is transferred to As(q) on the environmental map EMs through the mapping As, the orientation information on the pixel As(q) of the scene image on the environmental map EMs is expressed as As'(q,$\theta_q$), a pixel p of the eye image Ie is transferred to L(p) on the environmental map EMs common to the environmental map EMs through the mapping L, and the orientation information on the pixel L(p) of (the corneal-surface reflection image of) the eye image on the environmental map EMe is expressed as L'(p,$\theta_p$)).

Finally, the image registration device registers and aligns each pixel of the eye image Ie with the scene image Is by applying the mapping L( ), inverse mapping $R^{-1}$ of the rotational mapping R, and inverse mapping $As( )^{-1}$ (a warping function W ($W = As( )^{-1} \cdot R^{-1} \cdot L( )$) in FIG. 3) of the mapping As( ). That is, in the present embodiment, the question of the image registration boils down to a question of an alignment of two images on the environmental map. Hence, the number of parameters, which are necessary for the registration and should be obtained, is decreased. Therefore, the image registration device can perform the image registration (or image alignment) by only obtaining one pair of initial corresponding points (a pair composed of the feature point p and the feature point q). That is, in the image registration method performed with the image registration device, the performance of the correct registration can be achieved by only deciding (the position and local feature amount (orientation) of each feature point of) the pair of the initial corresponding points. In this context, the image registration (or image alignment) performed with the image registration device is robust. Even if plural initial corresponding point pairs are hardly extracted, the image registration device can correctly perform the registration as long as one pair of initial corresponding points is decided, and in this context the image registration method is robust. In the image registration device, techniques such as MSER (Maximally Stable External Regions) can be employed in addition to the SIFT and the SURF in order to detect the initial corresponding point pair and to calculate the local feature amount (for example, the orientation information) at each of points composing the initial corresponding point pair.

The aforementioned process performed by the image registration device, which decides "a single pair of initial corresponding points", has a novel feature. Hereinafter, the novel and distinguishing process of extracting the single pair of initial corresponding points is referred to as "RANRESAC" (RANdan RESAmple Consensus). In short, the RANRESAC is to decide one best-matched pair of initial corresponding points from plural candidate pairs of initial corresponding points for two images and perform the image registration method based on the best-matched pair of initial corresponding points. The RANRESAC differs largely from RANSAC (RANdom SAmple Consensus) which requires many pairs of proper (well-matched) corresponding points for the registration, in that the RANRESAC performs the image registration based on only one pair of optimal initial corresponding points. The two images to which the RANRESAC can be applied are not limited to a combination of the eye image and the scene image.

The image registration device and method will be described below with the image registration between (the corneal-surface reflection image of) the eye image and the scene image, as an example. However, the present invention is not limited to the eye image and the scene image, and the present invention can be applied to the mutual registration of various images.

3. Configuration of Image Registration Device

Figure 4:
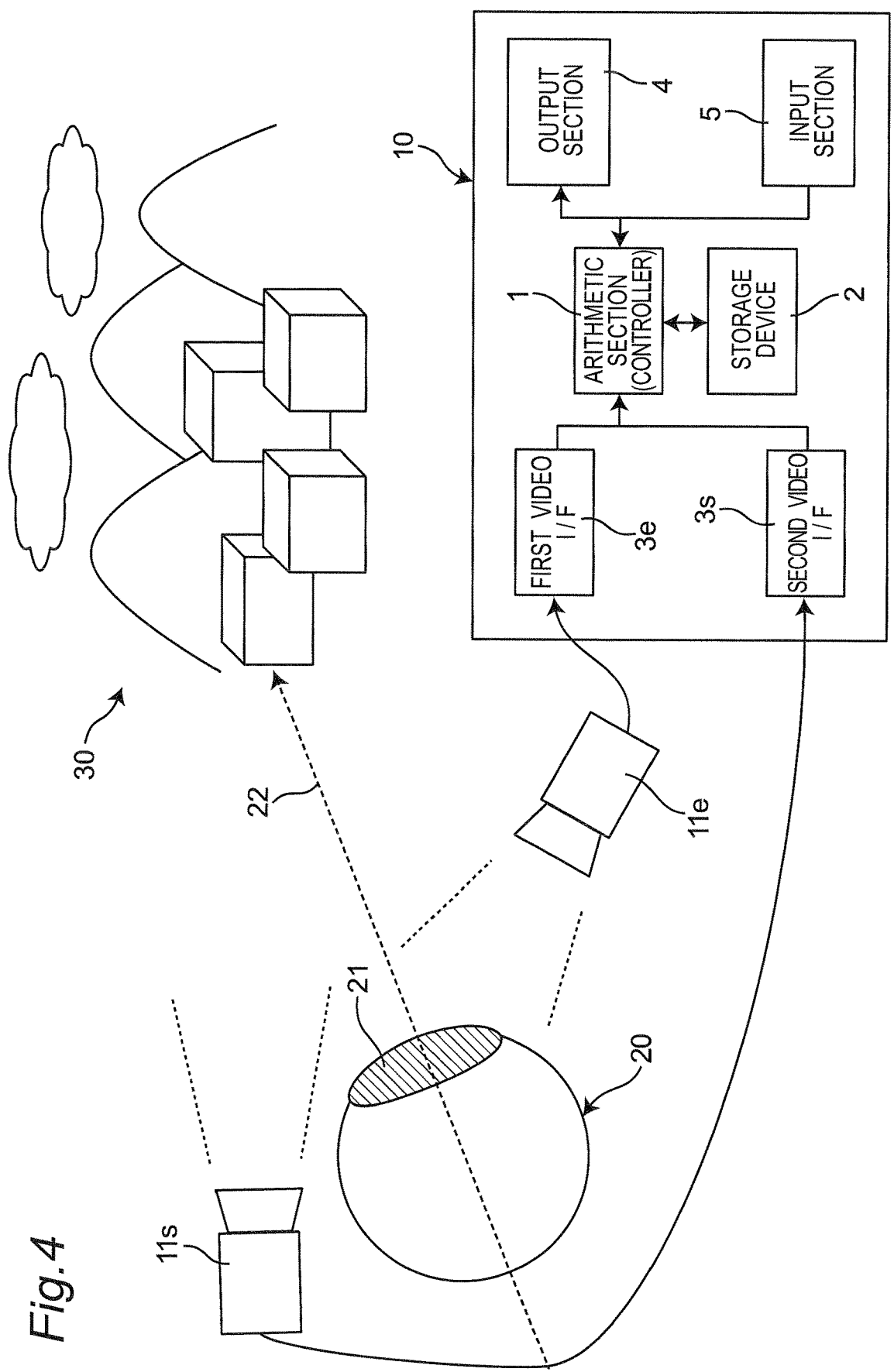
FIG. 4 is a block diagram illustrating a configuration of an image registration device of the embodiment.

FIG. 4 is a schematic diagram illustrating a configuration of an image registration device according to the embodiment of the present invention. The image registration device 10 includes a first video interface 3e and a second video interface 3s. The first video interface 3e obtains image data ("eye image" data) from an eye camera 11e that images (mainly a cornea 21 of) an eyeball 20 of the subject. The second video interface 3s obtains image data ("scene image" data) from a scene camera 11s that images the scene seen by the subject (the scene camera 11s is installed such that the imaging direction and a field angle are substantially aligned with (the optical axis direction of the eyeball of) the visual line direction of the subject (or such that the visual line direction is included)). The image registration device 10 further includes an arithmetic section 1 (controller) and a storage device 2. The arithmetic section 1 performs the image registration between the scene image and the eye image. The scene image and the eye image are input to the image registration device 10 through the first and second video interfaces 3e and 3s, and are stored in the storage device 2. Various pieces of data such as the eye image and the scene image data and a program executed with the arithmetic section 1 are stored in the storage device 2. The image registration device 10 composes an image registration system together with the eye camera 11e and the scene camera 11s.

The arithmetic section 1 executes a predetermined program (image registration program) to act as the mapping section, the corresponding point extractor, the rotational mapping deriver, and the registration section of the image registration device.

An input section 5 includes a data interface for an external arithmetic device and a user interface that receives data input from a user, and the user interface includes an input device such as a mouse and a keyboard.

The arithmetic section 1 also acts as the controller that controls operation of the whole device 10. The arithmetic section 1 may controls operations (such as the imaging) of the scene camera 11s and the eye camera 11e as one of the control operation.

The arithmetic section 1 is what is called a CPU (Central Processing Unit). However, the configuration of the arithmetic section 1 is not limited to the CPU and its surrounding auxiliary circuit. The arithmetic section 1 may be a GPU (Graphics Processing Unit) dedicated to predetermined arithmetic processing. Alternatively, the arithmetic section 1 may be implemented as processors such as an ASIC (Application Specific Integrated Circuit), a programmable logic device such as an FPGA (Field-Programmable Gate Array), and a microcontroller. The arithmetic section 1 may be provided by a combination of the plural elements such as the CPU, and elements composing the arithmetic section 1 are not limited to the above examples. The arithmetic section 1 executes an image registration program stored in the storage device 2 to carry out the image registration method of the embodiment. The image registration program may be recorded in a flexible disk, an optical disk, a flash memory, and the like, or transmitted through a network such as the Internet.

Various pieces of data and the image registration program executed by the arithmetic section 1 are stored in the storage device 2. For example, the storage device 2 is a RCM (Read-Only memory) and a RAM (Random Access Memory). In addition to the image registration program, the storage device 2 stores camera internal matrixes of the scene camera 11s and the eye camera 11e (the camera internal matrix is matrix-format data that includes a camera internal parameter as its element). The data of the camera internal matrix may be loaded and stored to the storage device 2 from the outside before the image registration. Alternatively the data of the camera internal matrix may be built in the image registration program. Alternatively, before the image registration, the image registration device 10 may calibrate the scene camera 11s and the eye camera 11e under control of the arithmetic section 1 (CPU) to obtain the camera internal matrix of each of the scene camera 11s and the eye camera 11e, and store the camera internal matrixes in the storage device 2.

The output section 4 outputs a result of the image registration performed with the arithmetic section 1. The output section 4 is, for example, a monitor display or a printer. Alternatively, the output section 4 may include an external storage device such as a hard disk drive and a flash memory or an interface mechanism that implements connection to another computer connected through a network.

4. Flow of Image Registration

With reference to FIGS. 5 to 14, processing executed by the arithmetic section 1 (see FIG. 4) of the image registration device 10 executing the image registration program will be described below.

Figure 5:
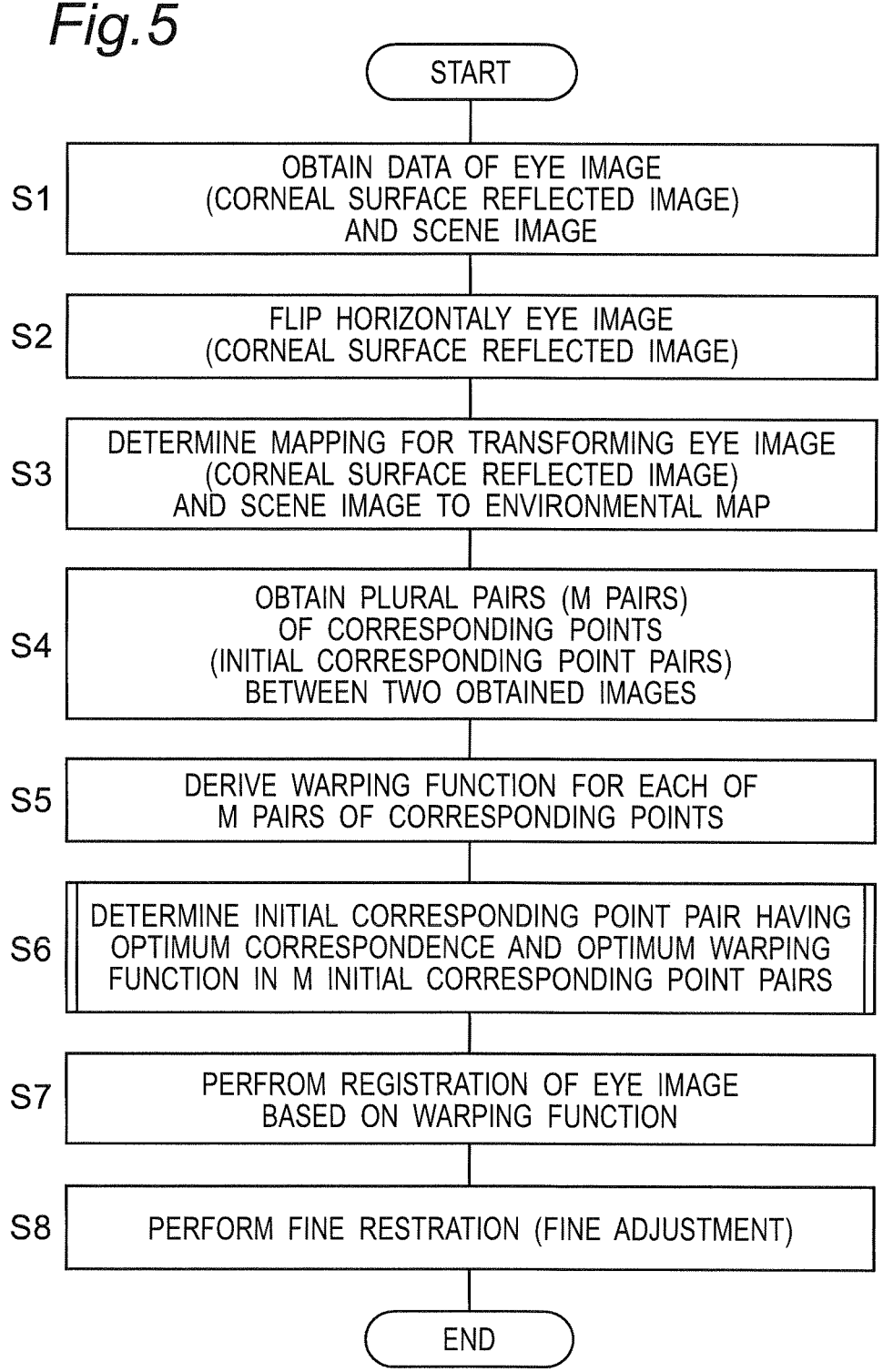
FIG. 5 is a flowchart illustrating a flow of image registration (or image alignment) processing performed by the image registration device.

FIG. 5 is a flowchart illustrating a flow of the image registration processing performed by the image registration device 10 (see FIG. 4).

In step S1, the arithmetic section 1 (see FIG. 4) which acts as the obtaining section obtains the eye image captured by the eye camera 11e and the scene image captured by the scene camera 11s. FIG. 6A illustrates an example of a scene image Is obtained in such a manner, and FIG. 6B illustrates an example of an eye image Ie' obtained similarly. The obtained scene image Is and eye image Ie' are stored in the storage device 2 (see FIG. 4).

In step S2, the arithmetic section 1 (see FIG. 4) which continuously acts as the obtaining section flips horizontally the obtained eye image Ie. Hence the orientation of the scene included in the corneal-surface reflection image of the eye image Ie is made matched with the orientation of the scene image Is. FIG. 6C illustrates an example of the horizontally-flipped eye image Ie. The horizontally-flipped eye image Ie is stored in the storage device 2 (see FIG. 4). Hereinafter, the arithmetic section 1 performs the processing using the horizontally-flipped eye image Ie. The image horizontally-flipping processing may be performed on the scene image Is instead of the eye image Ie.

In step S3, the arithmetic section 1 (see FIG. 4) which acts as the mapping section decides the mapping As( ) (see FIG. 3) which transfers the scene image Is to the environmental map EMs and the mapping L( ) (see FIG. 3) which transfers (the corneal-surface reflection image of) the eye image Ie to the environmental map EMe.

The mapping As( ) (see FIG. 3) which transfer the scene image Is to the environmental map EMs is decided as follows. The arithmetic section 1 (see FIG. 4) reads a 3×3 camera internal matrix Ks of the scene camera 11s, which is stored in the storage device 2 (see FIG. 4). The arithmetic section 1 decides the mapping As( ) according to the following equation.

$$A_s(q) = \frac{K_s^{-1}[q^T \ 1]^T}{\|K_s^{-1}[q^T \ 1]^T\|} \quad (1)$$

(where a vector q is a vector indicating a point (pixel) in the scene image Is. A point q in the scene image Is is transferred to a point on the environmental map EMs indicated by a vector As(q) through the mapping As( )) The arithmetic section 1 stores the mapping As( )(transform function) decided as above in the storage device 2.

On the other hand, the arithmetic section 1 decides mapping L( ) (see FIG. 3) which transfer the eye image Ie to the environmental map EMe in the following manner.

Figure 7A:
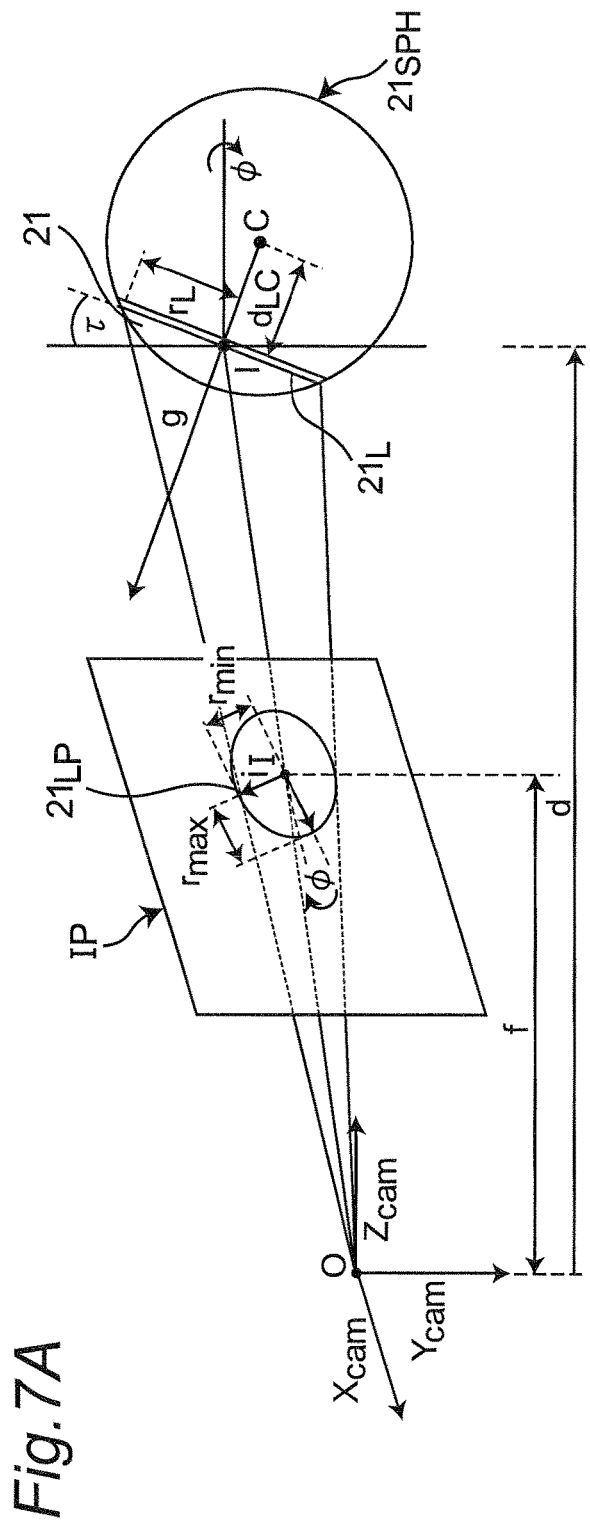
FIGS. 7A to 7C are views illustrating an eye pose estimation method in which a weak perspective projection model is used.
Figure 7C:
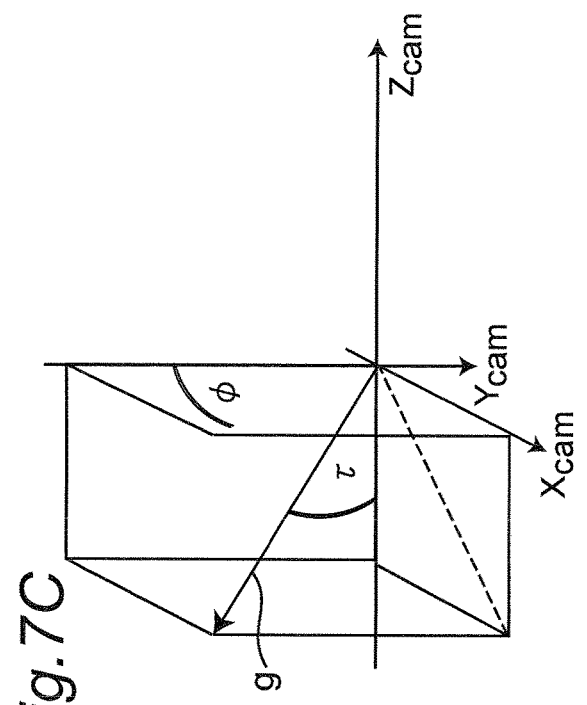
Figure 7B:
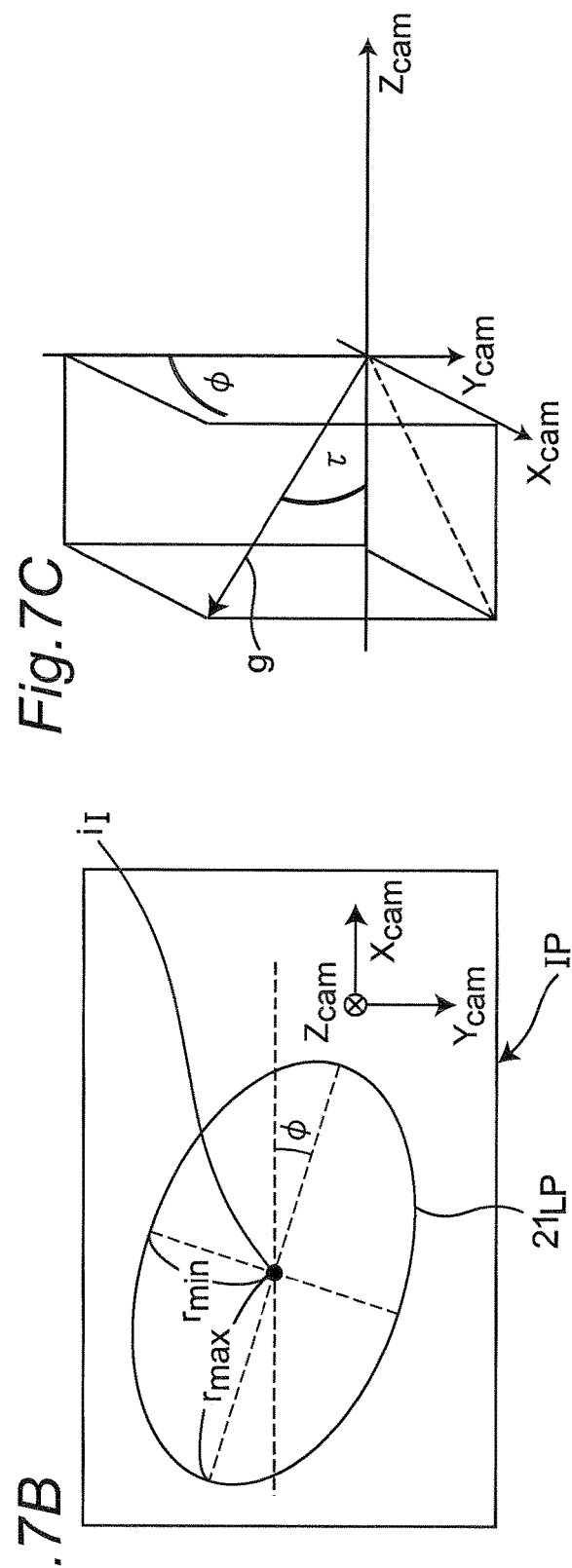

A method for deciding the mapping L( ) will be described below mainly with reference to FIGS. 7A-7C. FIG. 7A illustrates a weak perspective projection model of a non-rigid catadioptric imaging system composed of the cornea 21 considered to be a part of the spherical surface (the surface of the corneal sphere $21_{SPH}$) and the eye camera 11e (origin O). FIG. 7B illustrates an example of a projection surface IP when viewed from the origin O. FIG. 7C is a view illustrating a relationship among an optical axis direction vector g and angles φ and τ of the eyeball. In the weak perspective projection model, the cornea 21 can be considered to be a partial spherical surface which is obtained by cutting the corneal sphere $21_{SPH}$ by a corneal margin $21_L$. It is assumed that a fixed value (an average value of human being) is used as a typical dimension (a radius $r_L$, a distance d6 between a corneal margin center I and a center C of the spherical surface $21_{SPH}$) of the cornea 21.

The eyeball pose can be defined by the position of the corneal margin center I and the eyeball optical axis direction g. Assuming that the cornea 21 is sufficiently thin in a $Z_{cam}$-axis direction, the corneal margin $21_L$ that is a substantially perfect circle becomes an ellipse $21_L$ (including the perfect circle) on the projection surface IP. The ellipse $21_{LP}$ can be defined by four parameters, namely, a center $i_I$, a major axis $r_{max}$, a minor axis $r_{min}$, and a rotation angle φ. The center position of the corneal margin $21_L$ can be defined by a center $i_I$ of the ellipse $21_{LP}$ on the projection surface IP and a distance d ($d=r_L \cdot f/r_{max}$ (f is a focal distance)) between the cornea 21 and the camera (origin O). Assuming that a vector I is a position vector indicating the center of the cornea $21_L$, the vector I can be represented as $I=d \cdot K e^{-1} i_I$, where Ke is the 3×3 camera internal matrix of the scene camera 11s.

The eyeball optical axis direction g (that is substantially aligned with the visual line direction of the subject) can be represented as a direction vector $g=[\sin(\tau)\sin(\phi)-\sin(\tau)\cos(\phi)-\cos(\tau)]^T$. The angle τ is a gradient of the corneal margin $21_L$ with respect to an image forming surface (projection surface IP) of the eye camera 11e, namely, $\tau=\pm\arccos(r_{min}/r_{max})$, and the angle φ is a rotation angle of the ellipse $21_{LP}$ with respect to the image forming surface (see FIGS. 7A to 7C).

The position of the center C of the corneal sphere $21_{SPH}$ will be considered below. When the corneal sphere 21m has a radius $r_C$ of about 7.7 mm (the average of human being), it can be seen that the corneal sphere center C is located at the position away from the corneal margin center I by about 5.6 mm ($d_{LC}^2=r_C^2-r_L^2$) along a negative direction of the optical axis direction g.

In light of the above, an inverse light path (a path of a light which outputs from the pixel p in the eye image Ie, is reflected at the point P on the cornea 21, and travels toward a light source in the scene) of a path of light that forms the eye image Ie (see FIG. 6(c)) is considered based on the above fact. When Ke is the 3×3 camera internal matrix of the eye camera 11e (see FIG. 4), a normalized back projection vector Ae(p) of the eye camera 11e can be represented by the following equation, $$A_e(p) = \frac{K_e^{-1} p}{\|K_e^{-1} p\|} \quad (2)$$

where the vector p is a position vector of the pixel p in the eye image. When the light reflected at the point P on the cornea 21 forms the image iat the pixel p of the eye image, the position vector at the point P can be represented as $P=t_1 \times A_e(p)$. When C is the center of the corneal sphere $21_{SPH}$, a relational expression $\|\|P-C\|^2=r_C^2$ is solved with respect to $t_1$.

$$t_1^2 \|A_e(p)\|^2 - 2t_1(A_e(p) \cdot C) + \|C\|^2 - r_C^2 = 0 \quad (3)$$

Since $\|A_e(p)\|^2=1$ from the definition, the following equation is obtained.

$$t_1 = (A_e(p) \cdot C) \pm \sqrt{(A_e(p) \cdot C)^2 - \|C\|^2 + r_C^2} \quad (4)$$

Since the reflected light from the corneal surface is interested, a smaller one of two values of $t_1$ is used. Therefore, a specular point P on the cornea 21 is determined for the light incident on the pixel p of the eye image. A vector L(p) indicating the point in the scene in the path of the light incident on the pixel p of the eye image and a normal vector N(p) on the point P of the corneal surface are obtained by the following equation.

$$L(p) = 2(-A_e(p) \cdot N(p))N(p) + A_e(p) \quad (5)$$

$$N(p) = \frac{(P-C)}{\|P-C\|}$$

Using the above equation can specify a light source direction of the light reflected on the corneal surface with respect to the eye image Ie in pixels of at least pupil region. That is, the environmental map EMe (see FIG. 3) with respect to the corneal-surface reflection image can be constructed from the above equation. In other words, L( ) of the equation (5) is a mapping (transform function) to transfer the corneal-surface reflection image of the eye image Ie (see FIG. 6) to the environmental map of the non-rigid catadioptric imaging system.

The arithmetic section 1 (see FIG. 4) acts as the mapping section to perform the arithmetic operation corresponding to the equations (2) to (5), thereby deciding mapping L( ) (see FIG. 3) to transfer the corneal-surface reflection image of the eye image Ie to the environmental map EMe. A calculation algorithm used in the arithmetic operation is stored in the image registration program (where the vector p indicates the point (pixel) in the corneal-surface reflection image of the eye image Is, and the point p in the corneal-surface reflection image of the eye image Is is transferred to the point on the environmental map EMe indicated by the vector L(p) through the mapping L( )). The arithmetic section 1 stores the decided mapping L( ) in the storage device 2.

Figure 8:
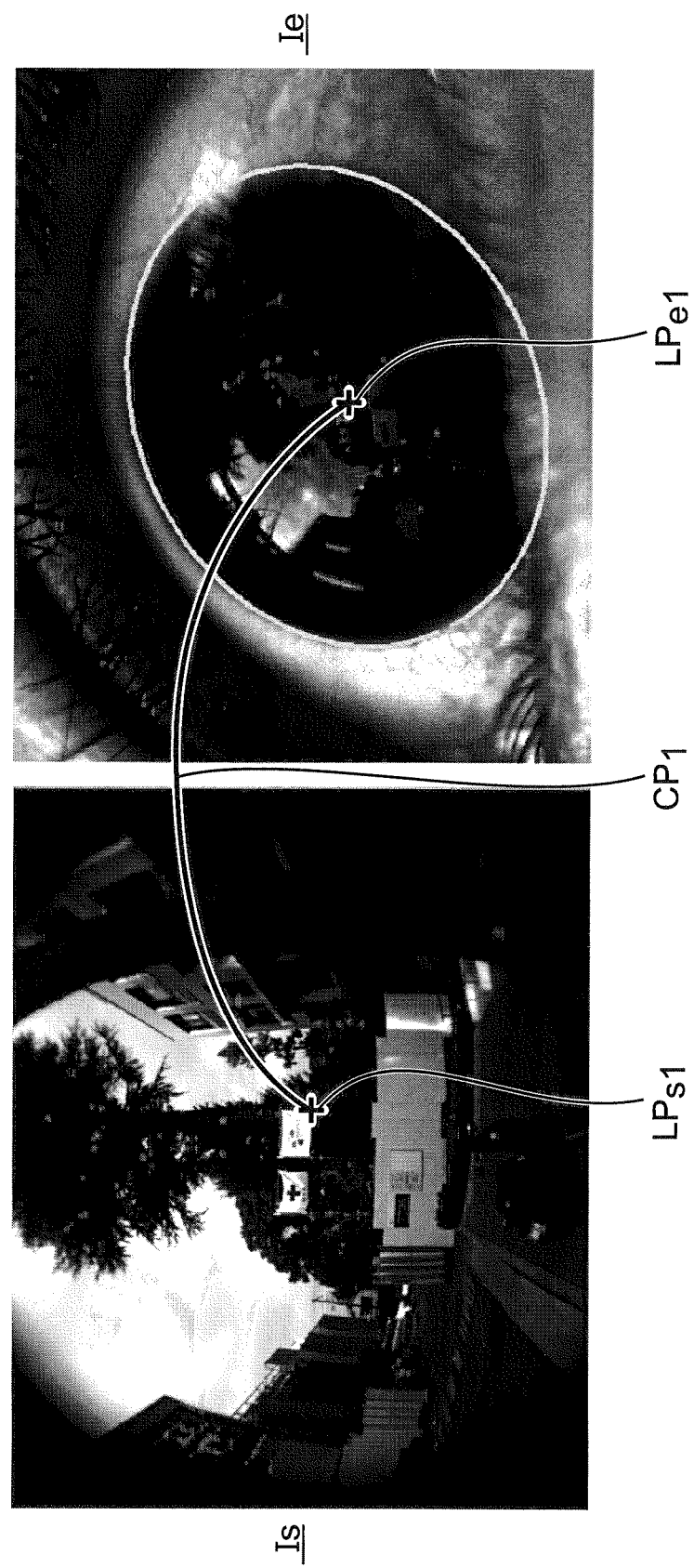
FIG. 8 is a view illustrating an example of an initial corresponding point pair in the eye image and the scene image.
Figure 9:
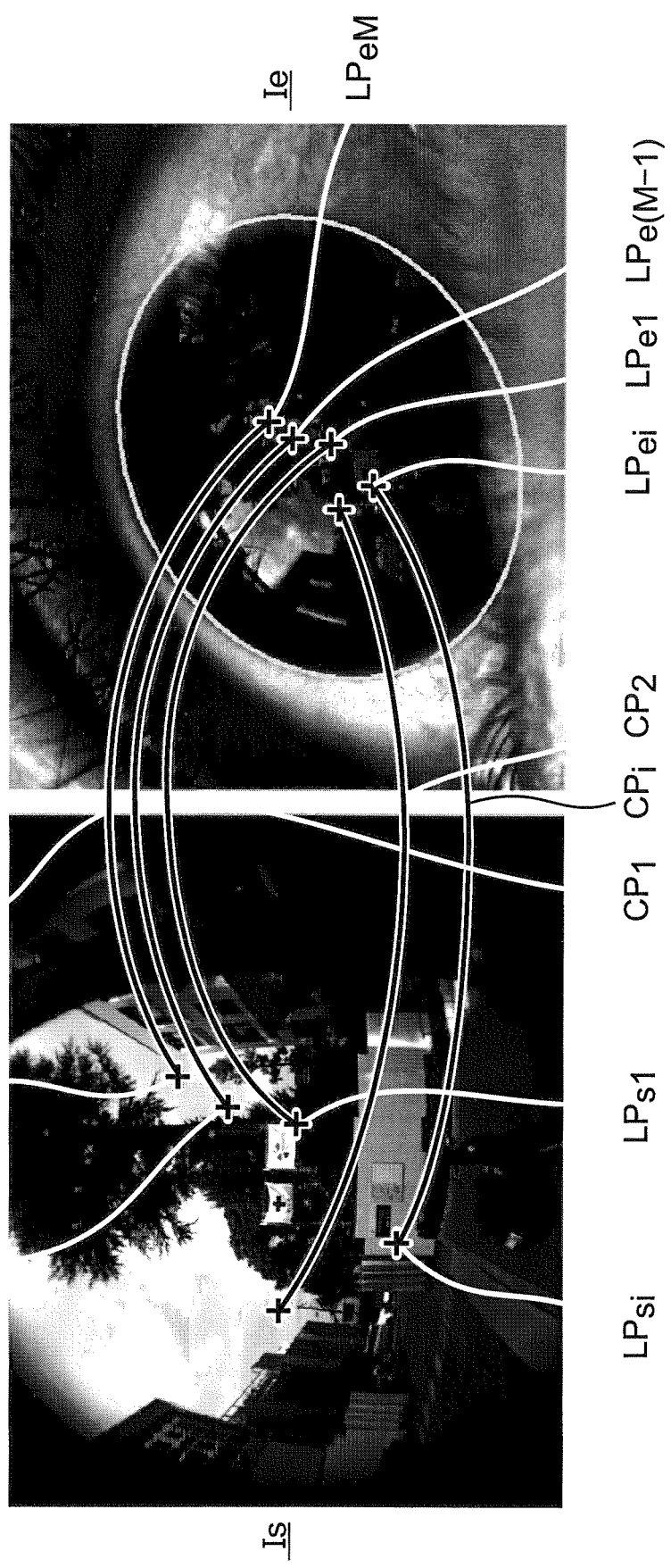
FIG. 9 is a view illustrating an example of plural sets of initial corresponding point pairs in the eye image and the scene image.

In step S4 of FIG. 5, the arithmetic section 1 acts as the corresponding point extractor to detect feature points (such as $LP_s1$ and $LP_e1$) which are not rotated and not scaled in the scene image Is (see FIG. 6A) and the eye image Ie (see FIG. 6C), and to calculate the local feature amount for each feature point as illustrated in FIGS. 8 and 9. For example, the detection of the feature point and the calculation of the local feature amount may be performed in accordance with the SIFT. Algorithms necessary for the detection of the feature point and the calculation of the local feature amount are stored in the image registration program stored in the storage device 2. When using the SIFT feature amount, the local feature amount calculated by the arithmetic section 1 includes four components, namely, 1. positional information (vector x), 2. orientation information ($\theta^x$), 3. feature vector (vector F(x)), and 4. scale parameter ($s^x$). Accordingly, for the local feature amount, an i-th feature point p of the eye image Ie can be expressed as follows.

$$\{(p_i, F(p_i), \theta_i^p, S_i^p) | i=1 \ldots M\}$$

$$\{p_i, F(p_i), \theta_i^p, S_i^p\}$$

An i-th feature point q of the scene image Is can be expressed as follows.

$$\{(q_i, F(q_i), \theta_i^q, S_i^q) | i=1 \ldots M\}$$

$$\{q_i, F(q_i), \theta_i^q, S_i^q\}$$

The arithmetic section 1 stores the position and local feature amount of the detected feature point in the storage device 2.

The arithmetic section 1 continues to act as the corresponding point extractor, and performs corresponding point matching (such as CP1) between the feature point (such as $LP_s1$) in the scene image Is and the feature point (such as $LP_s1$) in the eye image Ie based on the feature point detected by the SIFT, or the like and the calculated local feature amount. FIG. 8 illustrates a first initial corresponding point pair CP1. As illustrated in FIG. 9, the arithmetic section 1 performs the corresponding point matching plural times to obtain a plurality (M) of initial corresponding point pairs ($CP_1$ to $CP_M$). The arithmetic section 1 stores information about positions of the corresponding points ($LP_s1$ to $LP_sM$ and $LP_e1$ to $LP_eM$) and information about correspondence of the initial corresponding point pairs ($CP_1$ to $CP_M$) in the storage device 2.

In step S5, with respect to each of the initial corresponding point pairs ($CP_1$ to $CP_M$) obtained in step S4, the arithmetic section 1 derives (3×3 matrix) rotational mapping R for registering and aligning the scene image Is on the environmental map EMs and (the corneal-surface reflection image of) the eye image Ie on the environmental map EMe with each other, according to the following equation (6), based on the correspondence of the initial corresponding point pair ($CP_1$, $CP_2$, ... $CP_{M-1}$, or $CP_M$).

$$L(p) = RA_s(q) \quad (6)$$

Then, the arithmetic section 1 derives a transform function (warping function W) for registering the pixel of the eye image Ie with the pixel of the scene image Is using the rotational mapping R. In the equation (6), the vector p and the vector q indicate points ($LP_s1$, $LP_s2$, ..., $LP_sM-1$, or $LP_sM$ and $LP_e1$, $LP_e2$, ..., $LP_eM-1$, or $LP_eM$) of the scene image Is and eye image Ie composing the initial corresponding point pair ($CP_1$, $CP_2$, ..., $CP_{M-1}$, or $CP_M$). It is assumed that an optical system included in the scene camera 11s and an image formation system included in the eye camera 11e and the cornea 21 exist in the substantially same ray environment (the assumption causes the registration between the eye image Ie and the scene image Is (derivation of the warping function W) to reduce to derivation of the rotational mapping R).

The arithmetic section 1 derives the rotational mapping R according to the following calculation algorithm.

As can be seen from the equations (1) and (6) and FIG. 3, rotational mapping $R_i$ is represented as follows. The rotational mapping $R_i$ is expressed as shown below, in accordance with the correspondence of the initial corresponding point pair ($CP_i$) composed of the i-th corresponding point $LP_{si}$ of the scene image Is and the i-th corresponding point $LP_{ei}$ of the eye image Ie, $$R_i = [\hat{L}_x, \hat{L}_y, \hat{L}_z][\hat{A}_x, \hat{A}_y, \hat{A}_z]^{-1} \quad (7)$$

where $$\begin{aligned} L_x &= L(p_i) \\ L_y &= L(p_i) \times (L(p_i) \times L'(p_i, \theta_i^p)) \\ L_z &= L(p_i) \times L'(p_i, \theta_i^p) \\ L'(p, \theta_i^p) &= L(p + u(\theta^p)) - L(p) \end{aligned} \quad (8a)$$

$$\begin{aligned} A_x &= A_s(q_i) \\ A_y &= A_s(q_i) \times (A_s(q_i) \times A'_s(q_i, \theta_i^q)) \\ A_z &= A_s(p_i) \times (A'_s(q_i, \theta_i^q)) \\ A'_s(q, \theta_i^q) &= A_s(q + u(\theta^q)) - A_s(q) \end{aligned} \quad (8b)$$

$$u(\theta) = [\cos(\theta) \ \sin(\theta)]^T. \quad (8c)$$

A hat symbol "^" in the equation (7) expresses a normalized vector, and L'( ) and As'( ) are functions for transforming two-dimensionally-expressed orientation information into three-dimensional orientation information in the environmental map. Using the rotational mapping $R_i$ according to the correspondence of the i-th initial corresponding point pair ($CP_i$), the transform mapping (warping function $W_i$) is as shown below according to the correspondence of the ith initial corresponding point pair ($CP_i$) by the following equation (9).

$$W_i(p) \equiv \frac{\begin{bmatrix} 1 & 0 & 0 \\ 0 & 1 & 0 \end{bmatrix} K_s R_i^{-1} L(p)}{[0 \ 0 \ 1] K_s R_i^{-1} L(p)} \quad (9)$$

The warping function $W_i$ is a mapping to register the pixel of the eye image Ie with the pixel of the scene image Is according to the correspondence of the i-th initial corresponding point pair ($CP_i$). The arithmetic section 1 stores the warping function $W_i$ (i=1 to M) in the storage device 2, correlating the warping function $W_i$ (i=1 to M) with the initial corresponding point pair ($CP_1$ to $CP_M$).

Returning to FIG. 5, in step S6, the arithmetic section 1 (see FIG. 4) acting as the corresponding point pair extractor evaluates correspondence of each of M initial corresponding point pairs, and extracts an initial corresponding point pair composed of the most highly evaluated pair, as the corresponding point pair (RANRESAC processing). More specifically, in the RANRESAC processing, the arithmetic section 1 specifies plural secondary corresponding point pairs in the first and second images according to the correspondence of one of the initial corresponding point pairs, and evaluates correspondence of each secondary corresponding point pair so as to evaluate correspondence of the one of the initial corresponding point pairs. The arithmetic section 1 extracts the initial corresponding point pair including the most highly evaluated point pair, as the optimum initial corresponding point pair. That is, the arithmetic section 1 further obtains the secondary corresponding point pair in the eye image Ie and the scene image Is using the warping function $W_i$ obtained in step S5 according to the initial corresponding point pair ($CP_i$), calculates an image correlation associated with the secondary corresponding point pair, and evaluates correctness of the warping function $W_i$ so that the optimum warping function W is determined from the plural (M) warping functions $W_i$.

Figure 10:
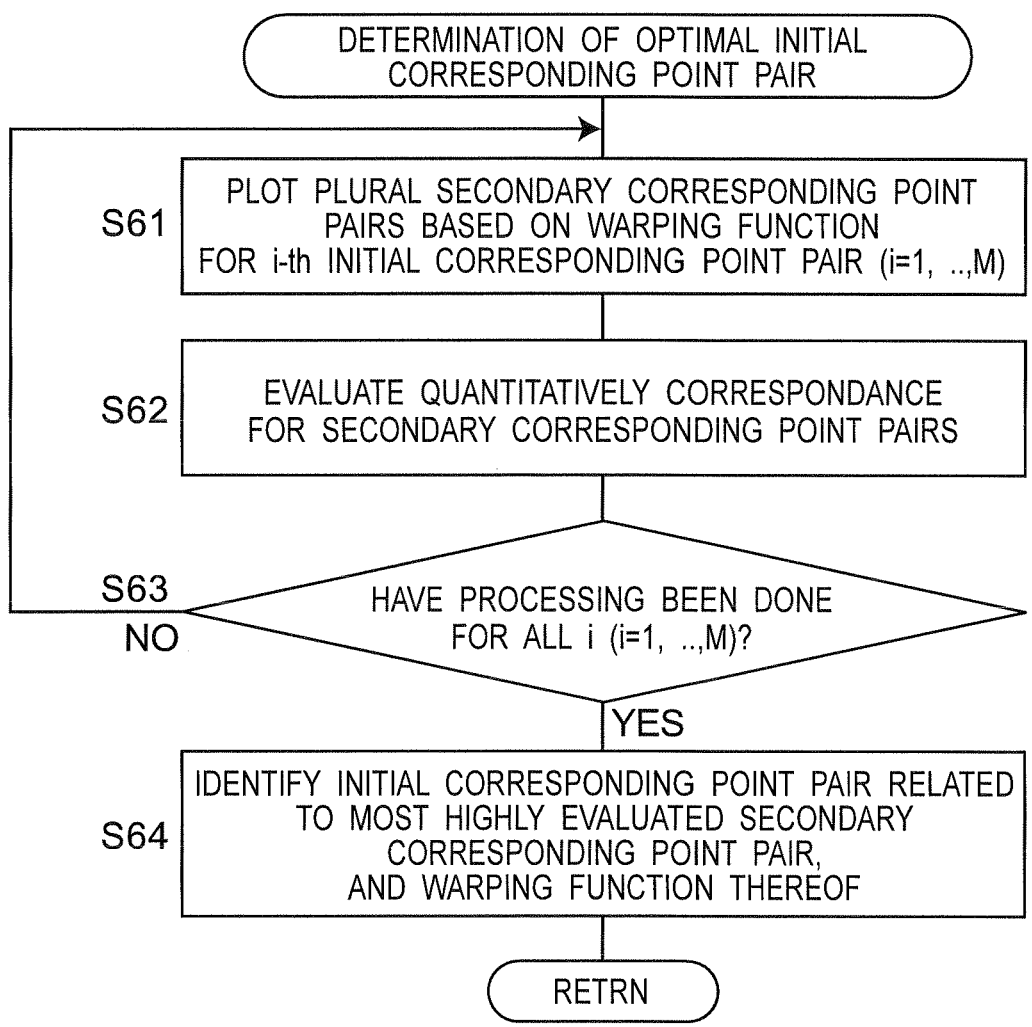
FIG. 10 is a flowchart illustrating detailed processing (RANRESAC processing) in step S5 of FIG. 5.

FIG. 10 is a flowchart illustrating the detailed processing (RANRESAC processing) of deciding the optimum initial corresponding point pair. The arithmetic section 1 acting as the corresponding point pair extractor performs processing in FIG. 10.

Figure 11:
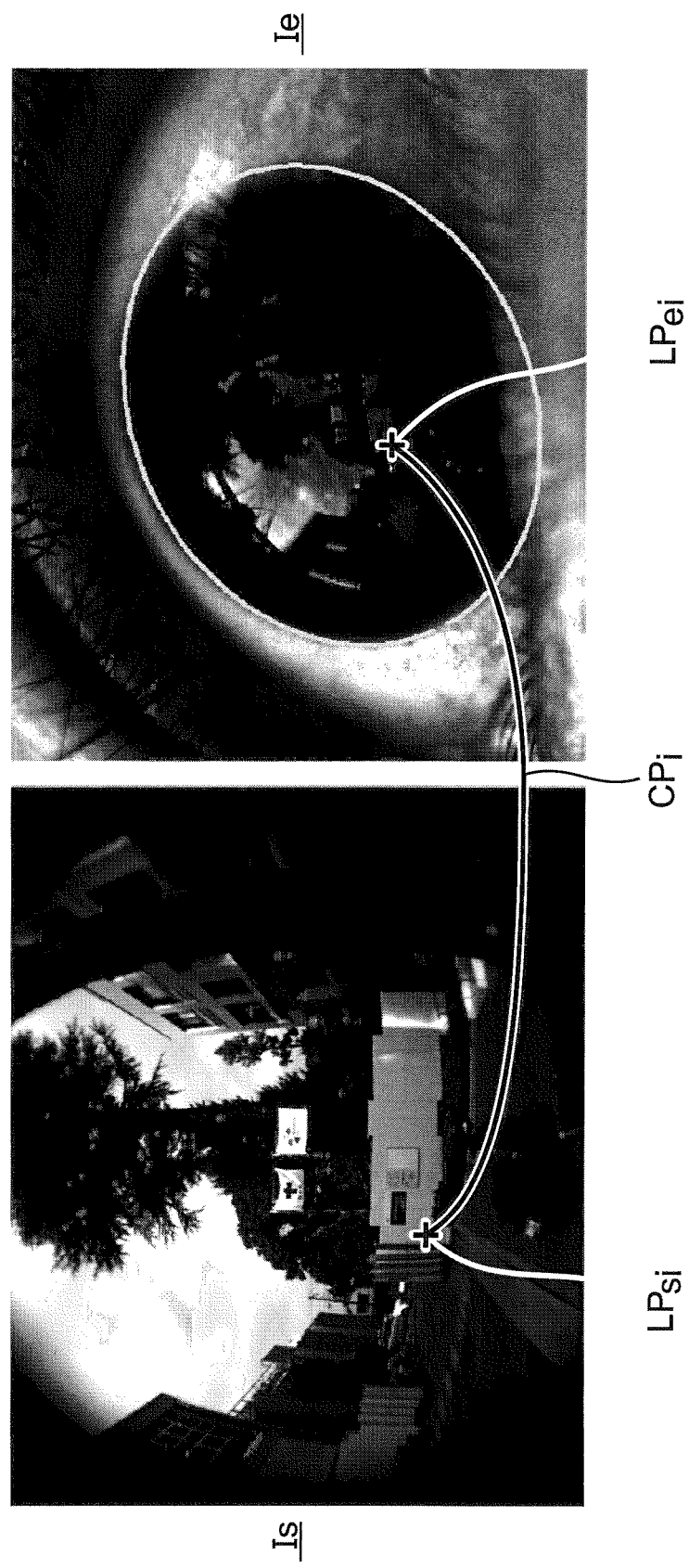
FIG. 11 is a view illustrating an i-th initial corresponding point pair.
Figure 12:
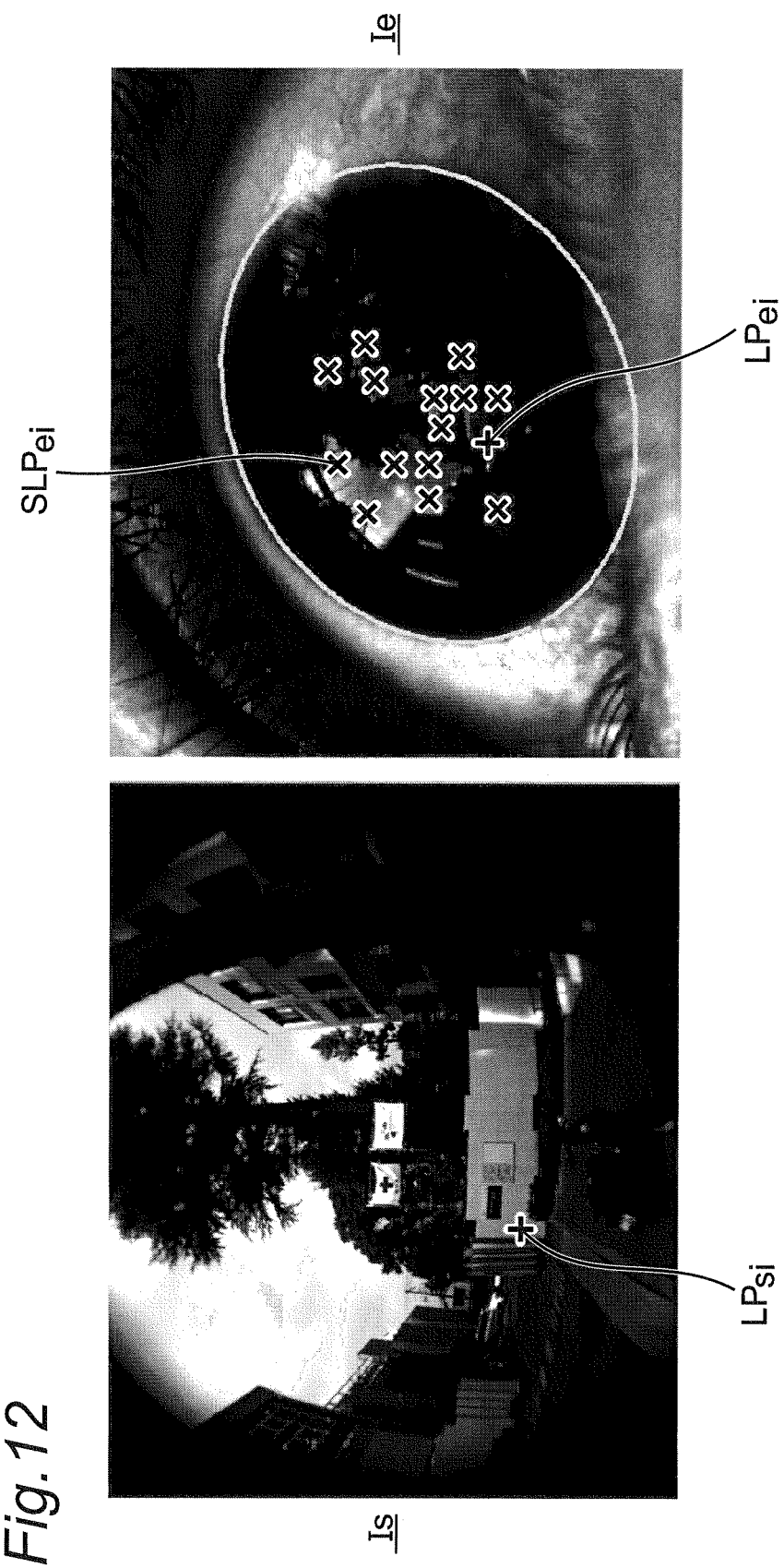
FIG. 12 is a view illustrating an example in which secondary corresponding points are randomly plotted in the eye image.
Figure 14:
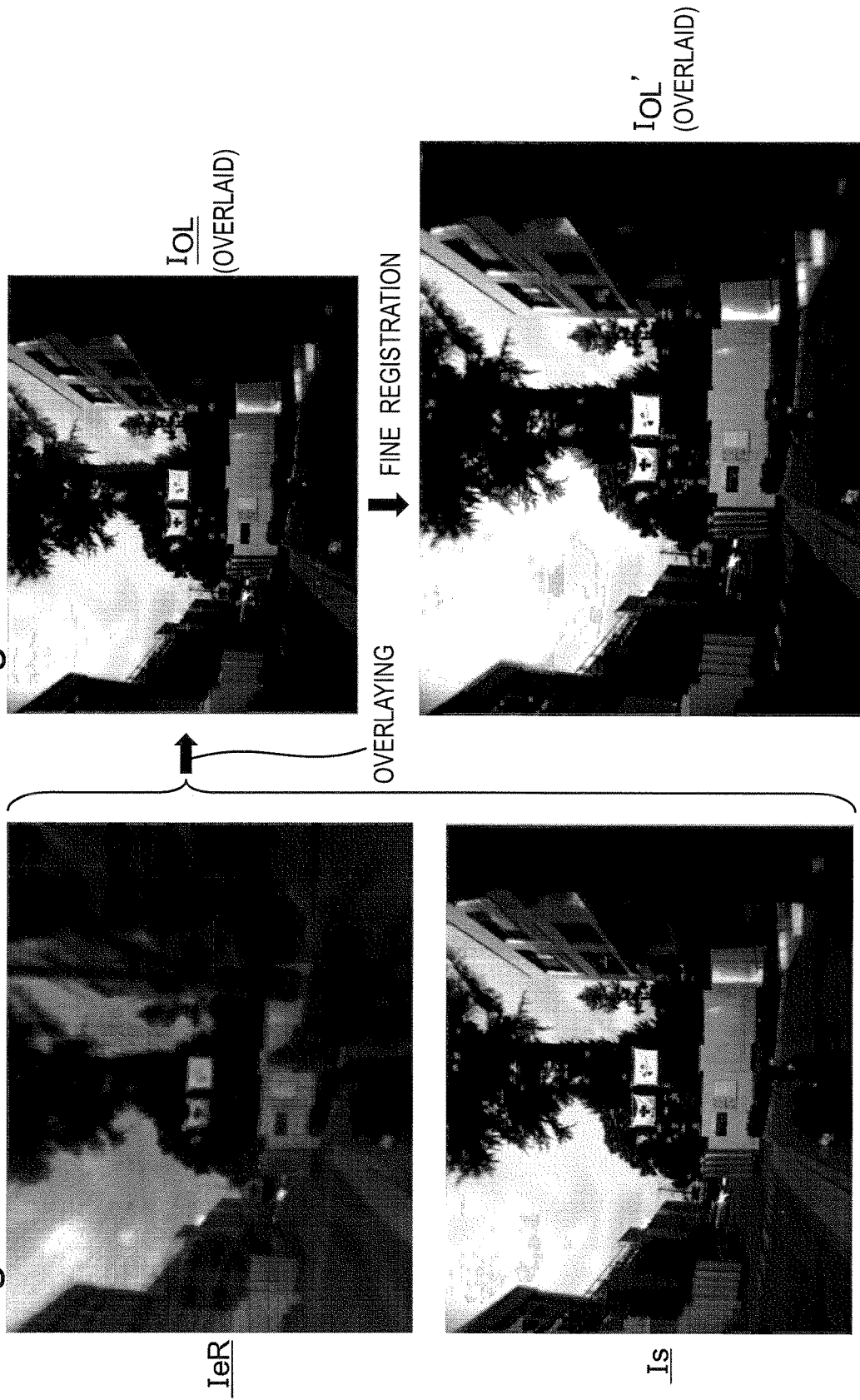
FIGS. 14A to 14D are views illustrating an example of the registered eye image and an example of performance of fine registration (fine-tune).

In step S61, the arithmetic section 1 acting as the corresponding point pair extractor generates a secondary corresponding point pair using the warping function $W_i$ obtained based on the i-th corresponding point pair $CP_i$ (see FIG. 11). Specifically, the arithmetic section 1 detects the corneal region of the eye image Ie and randomly sets K points $SLP_{ei}$ (see FIG. 12) in the corneal region. Then the arithmetic section 1 extracts a point $SLP_{si}$ (see FIG. 13) in the scene image Is corresponding to each of the K points $SLP_{ei}$ in the corneal region using the warping function $W_i$, and extracts K secondary corresponding point pairs. The secondary corresponding point pairs can also be represented as follows, $$\{(p_j^*, W_i(p_j^*)) | J = 1 \ldots K\}$$

where a vector $p_j^*$ is a positional vector indicating a point randomly selected in the corneal region of the eye image Ie.

In step S62, the arithmetic section 1 acting as the corresponding point pair extractor evaluates similarity among the secondary corresponding point pair group (the secondary corresponding point pair group obtained according to the warping function $W_i$ (i is a given integer (i=1 to M))) based on similarity in correlation and direction of a local texture. Specifically, the arithmetic section 1 evaluates the similarity using the following evaluation function.

$$P(W_i) = P_t(W_i) \cdot P_o(W_i) \propto -\sum_{j=1}^{K} \frac{\|F(p_j^*) - F(q_j^*)\|^2}{2\sigma_t^2} - \quad (10)$$

$$\alpha \sum_{j=1}^{K} \frac{\|1 - (\hat{L}'(p_j^*, \theta_{p_j^*}), \hat{A}_s'(q_j^*, \theta_{q_j^*}))\|^2}{2\sigma_o^2}$$

In the equation (10), a first term on the right side indicates the texture similarity, and a second term on the right side indicates the direction similarity. $\sigma_t$, $\sigma_o$, and $\alpha$ are positive constants defining weights of the texture correlation and the direction similarity. (*,*) is a vector inner product. $q_j^*$ indicates $W(p_j^*)$.

The arithmetic section 1 evaluates the secondary corresponding point pair group for each of the M initial corresponding point pairs using the equation (10) (step S63).

In step S64, the arithmetic section 1 acting as the corresponding point pair extractor identifies the secondary corresponding point pair group having the most highly evaluated similarity, namely, an i'-th initial corresponding point pair ($CP_{i'}$) defined by the following equation (11) and its warping function $W_{i'}$.

$$i' = \underset{i}{\mathrm{argmax}}(P(W_i)) \quad (11)$$

It is important to properly set a scale parameter for a local feature at each point composing the secondary corresponding point pair. Ideally, the scale parameter may be adjusted so as to occupy the same size (spatial volume) in the environmental map. A ratio of the scale parameter at the point (p,q) of each image is obtained according to the equation (12), $$s_i^q = \frac{1}{2\sqrt{2}} \|W_i(p + [1 \ 1]^T) - W_i(p - [1 \ 1]^T)\| \cdot s_i^p \quad (12)$$

where $s_i^p$ is the scale parameter set by a user in the corneal-surface reflection image, and $s_i^q$ is the scale parameter at the point q in the corresponding scene image.

In step S7 of FIG. 5, the arithmetic section 1 acting as the registration section, registers and aligns (the corneal-surface reflection image of) the eye image Ie with the scene image Is using the warping function $W_{i'}$ decided in step S6 to generate data of the registered and aligned eye image. FIG. 14A illustrates (the corneal-surface reflection image of) a registered and aligned eye image IeR obtained in step S7.

In step S8 of FIG. 5, the arithmetic section 1 acting as the registration section finely adjusts the warping function $W_{i'}$ decided in step S6 (fine registration). The data of the finely-adjusted eye image is stored in the storage device 2 (see FIG. 4). In this step, the arithmetic section 1 repeatedly performs the evaluation according to the equation (10) while minutely varying the position (see FIG. 7) of the center C of the corneal sphere, namely, the distance $d_{LC}$ and the rotation angle φ of the ellipse in the projection surface IP, so that an evaluation value converges. An interior point method is adopted in the convergence. FIG. 14C illustrates an image which is obtained by overlaying the pre-fine-registration image IeR on the scene image Is. FIG. 14D illustrates an image which is obtained by overlaying the post-fine-registration image IeR on the scene image Is. As can be seen from FIGS. 14C and 14D, accuracy of the registration is further improved through the fine registration processing.

In this manner, the image registration device 10 (see FIG. 4) can decide the transform mapping (warping function $W_i(\ )$) based on the only one pair of corresponding point pairs (the optimum initial corresponding point pair decided in step S6). Therefore, the registration of the eye image Ie with the scene image Is can be performed robustly. Additionally, the image registration device 10 (see FIG. 4) can perform the RANRESAC processing to properly decide only one pair of corresponding points. In short, the image registration device can properly decide one pair of initial corresponding points through the RANRESAC processing, and correctly perform the registration. In view of this, the image registration performed by the image registration device is robust. Even if plural initial corresponding point pairs are hardly extracted, the image registration device can correctly perform the registration as long as one pair of initial corresponding points is decided. In view of this, the image registration method is also robust.

In the embodiment, by way of example, the eye image Ie is registered and aligned with the scene image Is. Alternatively, the scene image Is may be registered and aligned with the eye image Ie. Images that can be registered and aligned by the image registration device 10 of the embodiment is not limited to the combination of the eye image Ie and the scene image Is. In the above embodiment, the image registration device 10 obtains data of image to be registered and aligned from the imaging device (the eye camera 11e and the scene camera 11s (see FIG. 4)) connected to the image registration device 10. However, the image registration device 10 can obtain data of one or at least two images from a device (such as an image database) except for such an imaging device, and perform the registration on the obtained image(s). For example, the image registration device 10 may obtain image data from an open database such as Google Street View through a network, and perform the registration between the obtained image and the eye image Ie (see FIG. 6) captured by the eye camera 11e. Alternatively, the image registration device 10 may obtain plural pieces of image data from one or plural external devices (such as an image database) and recording media such as an optical disk and a flash memory, and perform the registration between the plural images. In such cases, the image registration device 10 may properly prepare the mapping to transfer each obtained image to the environmental map prior to the image registration processing. The preparation method is well known to those skilled in the art.

In the image registration device 10, the image registration program is stored in the storage device 2 (see FIG. 4), and the calculation algorithm necessary for the calculation of the above quantities is included in the image registration program (However, a part or whole of the calculation algorithm may be stored in the storage device 2 independently of the image registration program).

5. Experimental Result

A result of experiment conducted by the image registration device 10 (see FIG. 4) of the embodiment will be described below. In the experiment, in order to stably and simultaneously photograph a corneal-surface reflection image (eye image Ie) and a scene image Is, a system was configured to include two compact board cameras (IDS UI-1241LE-C-HQ, 1/1.8" CMOS, 1280×1024 pixel) and a head mount system as the eye camera 11e (see FIG. 4) and the scene camera 11s (see FIG. 4). In the system, the eye camera 11e (f=12 nm, (H, V)=(33.3, 24.8) deg) was located away from the eyeball 20 by about 70 to 110 nm, and shot images with a pupil diameter of about 400 to 450 pixels. A gain and an exposure parameter of the eye camera 11e were adjusted under a low light intensity environment. The eye camera 11e and the scene camera 11s were connected to the image registration device 10 (PC (Personal Computer)) and shot images at a rate of 10 fps.

The data were obtained for each of four subjects. For each subject, the data were obtained at three places in both indoor and outdoor environments. After the data of four subjects were obtained, a frame including closed lid was removed manually, and then a pupil contour was extracted in each 10 frames.

The experiment was performed by the PC implementing the image registration method (1-point RANRESAC) of the embodiment and 2-point RANSAC and 2-point RANRESAC for the purpose of comparison.

In the 2-point RANSAC, two pairs were randomly selected from the initial corresponding point pairs, and the warping function was estimated from the two pairs of initial corresponding points. Then, how many pairs were able to be correctly registered was counted using the remaining pairs of initial corresponding points. These operations were repeated 500 times. Then, the best solution in the obtained solutions (warping functions) was decided as the warping function.

In the 2-point RANRESAC, the warping function was estimated similarly to the 2-point RANSAC. Then, the evaluation was performed according to the RANRESAC method. Similarly to the 2-point RANSAC, the best solution was selected from results of the 500-time repetition.

In all the experiments, a SURF local feature implemented in a Computer Vision System Toolbox of MATLAB 2013b was used, and a PC (Intel Core i7 3.2 GHz, 16 GB RAM) was used. $(\sigma_t, \sigma_o, \alpha, s^P)=(0.2, 0.2, 0.3, 0.5)$ was set as the parameter. The random-sampling point number (the number of pairs of corresponding points) K was set to 200 in the method (1-point RANRESAC) of the embodiment and the 2-point RANRESAC.

Tables 1 to 7 illustrate accuracy (success rate) of the registration. Time necessary for the registration was 37.0 seconds per frame (the image registration method (1-point RANRESAC) of the embodiment), 14.47 seconds per frame (2-point RANSAC), and 180.47 seconds per frame (2-point RANRESAC).

TABLE 1

Experimental result under outdoor environment 1

| Scene name | Subject number | The number of tested frames | with the Method of the Embodiment | 2-Point RANSAC | 2-Point RANRESAC |
|---|---|---|---|---|---|
| Campus 1 | 1 | 16 | 16 (100%) | 3 (18.8%) | 13 (81.25%) |
| Campus 1 | 2 | 26 | 21 (80.8%) | 2 (7.7%) | 10 (38.5%) |
| Campus 1 | 3 | 23 | 22 (94.7%) | 1 (4.35%) | 4 (17.39%) |
| Campus 1 | 4 | 25 | 23 (92.0%) | 1 (4.0%) | 4 (16.0%) |

TABLE 2

Experimental result under outdoor environment 2

| Scene name | Subject number | The number of tested frames | with the Method of the Embodiment | 2-Point RANSAC | 2-Point RANRESAC |
|---|---|---|---|---|---|
| Campus 2 | 1 | 46 | 41 (89.1%) | 2 (4.4%) | 9 (39.1%) |
| Campus 2 | 2 | 20 | 16 (80.0%) | 2 (10.0%) | 8 (34.7%) |
| Campus 2 | 3 | 23 | 21 (91.3%) | 3 (13.0%) | 8 (34.8%) |
| Campus 2 | 4 | 23 | 17 (73.9%) | 2 (8.7%) | 7 (15.2%) |

TABLE 3

Experimental result under outdoor environment 3

| Scene name | Subject number | The number of tested frames | with the Method of the Embodiment | 2-Point RANSAC | 2-Point RANRESAC |
|---|---|---|---|---|---|
| Road | 1 | 25 | 25 (100.0%) | 1 (4.0%) | 9 (36.0%) |
| Road | 2 | 23 | 20 (87.0%) | 0 (0%) | 3 (13.4%) |
| Road | 3 | 30 | 26 (86.7%) | 3 (10.0%) | 6 (20.0%) |
| Road | 4 | 25 | 23 (92.0%) | 2 (8.0%) | 8 (32.0%) |

TABLE 4

Experimental result under indoor environment 1

| Scene name | Subject number | The number of tested frames | with the Method of the Embodiment | 2-Point RANSAC | 2-Point RANRESAC |
|---|---|---|---|---|---|
| Lobby 1 | 1 | 25 | 18 (72.0%) | 1 (4.0%) | 10 (40.0%) |
| Lobby 1 | 2 | 22 | 19 (86.4%) | 1 (4.6%) | 11 (50.6%) |
| Lobby 1 | 3 | 25 | 23 (92.0%) | 3 (12.0%) | 10 (40.0%) |
| Lobby 1 | 4 | 29 | 29 (100.0%) | 2 (6.9%) | 15 (51.7%) |

TABLE 5

Experimental result under indoor environment 2

| Scene name | Subject number | The number of tested frames | with the Method of the Embodiment | 2-Point RANSAC | 2-Point RANRESAC |
|---|---|---|---|---|---|
| Lobby 2 | 1 | 24 | 21 (87.5%) | 2 (8.3%) | 13 (54.2%) |
| Lobby 2 | 2 | 24 | 23 (95.8%) | 1 (4.2%) | 11 (45.8%) |
| Lobby 2 | 3 | 28 | 27 (96.4%) | 2 (7.14%) | 15 (53.57%) |
| Lobby 2 | 4 | 26 | 26 (100.0%) | 2 (7.7%) | 9 (34.6%) |

TABLE 6

Experimental result under indoor environment 3

| Scene name | Subject number | The number of tested frames | with the Method of the Embodiment | 2-Point RANSAC | 2-Point RANRESAC |
|---|---|---|---|---|---|
| Indoor | 1 | 25 | 9 (52.94%) | 0 (0%) | 3 (17.7%) |
| Indoor | 2 | 26 | 20 (76.9%) | 2 (7.69%) | 9 (34.6%) |
| Indoor | 3 | 26 | 20 (76.9%) | 2 (7.69%) | 5 (19.23%) |
| Indoor | 4 | 24 | 18 (75.0%) | 1 (4.2%) | 5 (20.8%) |

TABLE 7

Summary of experimental results

| Total | | | |
|---|---|---|---|
| The number of tested frames | with the Method of the Embodiment | 2-Point RANSAC | 2-Point RANRESAC |
| 626 | 538 (85.9%) | 41 (6.6%) | 200 (32.0%) |

According to the image registration method of the present embodiment, the success rate is 85.5% (Tables 1 to 3) in the outdoor scene and it is 86.3% in the indoor scene (Tables 4 to 6), so that the success rate of the image registration method of the present embodiment is much better than that of the 2-point RANSAC and the 2-point RANRESAC. As to the success rate, the 2-point RANRESAC is not better than the 1-point RANRESAC (the present embodiment), but is better than the 2-point RANSAC which performs the same rotating matrix estimation. Therefore, it can be confirmed that the RANRESAC method is robust against noise situation.

6. Applications

The image registration device and image registration method of the embodiment enable matching the corneal-surface reflection image of the eye image Ie and the scene image Is with each other. Applications using concepts of the present embodiment will be described below.

6.1. Estimation of Gazing Point

Gazing point estimation with the image registration device of the embodiment will be described below. With the gazing point estimation, for example, an image of a scene seen by a user is extracted, and an object or a place which is seen by the user can be identified by referring to an image of the Google Street View. For example, this technology can be applied to an AR (Augmented Reality) system. In the gazing point estimation with the image registration device of the embodiment, unlike a conventional device, it is not necessary to calibrate a relative positional relationship between the eye camera and the scene camera. Additionally, it is not necessary to fix the relative positional relationship.

First the arithmetic section 1 acting as the viewpoint extractor detects a gazing reflection point GRP (see FIG. 15) of the subject by detecting the pose of the eyeball from the eye image by a known technique. As used herein, the gazing reflection point GRP means a point at which the light arriving from the visual line direction substantially aligned with the optical axis of the eyeball of the subject is reflected by the corneal surface (for example, International Patent Publication WO2014/021169A1 is referred to for more information about the known technique). The arithmetic section 1 derives the warping function W for registering the eye image Ie with the scene image Is. Finally, the arithmetic section 1 obtains a point GRP' (see FIG. 15) corresponding to the gazing reflection point GRP of the eye image Ie in the scene image Is. The point GRP' in the scene image Is corresponds to the scene (gazing point) gazed by the subject.

Thus, the image registration device of the embodiment can extract the scene (gazing point) gazed by the subject from the scene image Is. That is, the image registration device of the embodiment also acts as a gazing point extraction system.

6.1.1 Application to Display Device

A display device using the image registration device acting as the gazing point extraction system will be described below. This technology can be applied to, for example, an AR (Augmented Reality) system. In the display device (AR system), unlike a conventional device, it is not necessary to calibrate the relative positional relationship between the eye camera and the scene camera. Additionally, it is not necessary to fix the relative positional relationship. The display device includes the configuration shown in FIG. 4 similarly to the image registration device of the embodiment. The output section 4 is a monitor display that displays an image. The arithmetic section 1 causes the output section 4 to display the scene image Is, and causes the output section 4 to display a predetermined image superposed on any position in the extracted scene image Is. Therefore, the AR system can perform superposed display.

6.2. Estimation of Peripheral Visual Field

The image registration device and image registration method of the embodiment can restore the peripheral visual field of the subject in the scene image Is.

The arithmetic section 1 acting as the visual field estimator identifies pose (optical axis) of the eyeball using the eye image Ie, and identifies points at which light arriving from the direction having a predetermined angle (for example, 10, 20, . . . , 90 degrees) with respect to the optical axis of the eyeball is reflected by the corneal surface (see FIG. 16). These points are distributed so as to draw a curve in the eye image Ie. Then, the arithmetic section 1 detects points corresponding to the points from the scene image Is using the warping function W decided in the embodiment. The detected points form a region of the peripheral visual field of the subject (a region expanding with a predetermined angle around the gazing point).

Thus, the image registration device of the embodiment can extract the region of the peripheral visual field of the subject from the scene image Is. The image registration device can estimate the region of the peripheral visual field of the subject in the scene image Is. That is, the image registration device also acts as the peripheral visual field estimation system.

6.3. Application to Iris Recognition

In an existing iris recognition technique, the eye image is obtained using infrared light in order to suppress the specular reflection on the corneal surface. On the other hand, with the image registration device of the embodiment, the specular reflection (corneal-surface reflection image) included in the eye image can be removed using the scene image.

The arithmetic section 1 of the image registration device of the embodiment derives the warping function W between the eye image Ie (see FIG. 17) and the scene image Is (see FIG. 17). The arithmetic section 1 registers and aligns the scene image Is with the eye image Ie using the warping function W. The arithmetic section 1 acting as an iris image generator subtracts the registered and aligned scene image Is from a portion of the eye image Ie corresponding to the registered and aligned scene image Is, thereby removing the corneal-surface reflection image of the eye image Ie to generate the iris image. An image $I_{it}$ in FIG. 17 is an eye image in which the corneal specular reflection is effectively removed, namely, an iris image. Thus, according to the image registration device of the embodiment, the corneal specular reflection included in the eye image Ie can effectively be removed, so that the iris image $I_{it}$ without noise can be obtained. Therefore, it is not necessary to use the infrared light in the lighting in order to suppress the specular reflection in the corneal surface. Then, the arithmetic section 1 acting as the recognizer performs iris recognition processing on the iris image using a known method.

In this way, according to the image registration device of the embodiment, even if the eye image is obtained using lighting of visible light region in addition to an infrared lighting, the corneal specular reflection can effectively be removed, thereby obtaining a high accurate iris image. Using the iris image obtained in such a manner can improve accuracy of iris recognition. That is, the image registration device of the embodiment acts as the iris recognition system.

In view of the above, the embodiment also discloses the following systems and methods.

(1) A gazing point extraction system including:

an obtaining section configured to obtain a first image including an image of an eyeball of a subject and a second image including an image of an object in a visual line direction of the subject;

a mapping section configured to decide a first mapping for transforming the first image to an environmental map, and a second mapping for transforming the second image to an environmental map;

a corresponding point pair extractor configured to extract a pair of corresponding points by detecting one point in the first image and one point in the second image which corresponds to the one point in the first image;

a rotational mapping deriver configured to derive a rotational mapping for registering an image of the first image in the environmental map and an image of the second image in the environmental map with each other, based on positions and local feature amounts of the one point in the first image and the one point in the second image, the one point in the first image and the one point in the second image composing the pair of corresponding points; and a viewpoint extractor configured to detect a gazing reflection point on the first image by detecting a pose of the eyeball from the first image, and to obtain, as a point gazed by the subject, a point corresponding to the gazing reflection point in the second image based on the first mapping, the rotational mapping, and the second mapping.

(2) A display system (AR system) including the gazing point extraction system of (1).

(3) A peripheral visual field estimation system including:

an obtaining section configured to obtain a first image including an image of an eyeball of a subject and a second image including an image of an object in a visual line direction of the subject;

a mapping section configured to decide a first mapping for transforming the first image to an environmental map, and a second mapping for transforming the second image to an environmental map;

a corresponding point pair extractor configured to extract a pair of corresponding points by detecting one point in the first image and one point in the second image which corresponds to the one point in the first image;

a rotational mapping deriver configured to derive a rotational mapping for registering an image of the first image in the environmental map and an image of the second image in the environmental map with each other, based on positions and local feature amounts of the one point in the first image and the one point in the second image, the one point in the first image and the one point in the second image composing the pair of corresponding points; and a visual field estimator configured to identify an optical axis of the eyeball from the first image, identify reflection points at which lights arriving from directions having predetermined angles with respect to the optical axis is reflected by a corneal surface, and detect reflection points identified from the second image, as a group of points composing a region of a peripheral visual field of the subject, based on the first mapping, the rotational mapping, and the second mapping.

(4) An iris recognition system including:

an obtaining section configured to obtain data of a first image including an image of an eyeball of a subject and a second image including an image of an object in a visual line direction of the subject;

a storage device configured to store the data of the first image and the data of the second image;

a mapping section configured to decide a first mapping for transforming the first image to an environmental map, and a second mapping for transforming the second image to an environmental map;

a corresponding point pair extractor configured to extract a pair of corresponding points by detecting one point in the first image and one point in the second image which corresponds to the one point in the first image;

a rotational mapping deriver configured to derive a rotational mapping for registering an image of the first image in the environmental map and an image of the second image in the environmental map with each other, based on positions and local feature amounts of the one point in the first image and the one point in the second image which compose the pair of corresponding points; and a registration section configured to register the data of the first image stored in the storage device with the data of the second image stored in the storage device in order to generate data of the first image registered with the second image, based on the first mapping, the rotational mapping, and the second mapping;

an iris image generator configured to generate an iris image by subtracting the registered first image from the second image; and a recognizer configured to perform iris recognition with the iris image.

(5) A gazing point extraction method including the steps of:

obtaining a first image including an image of an eyeball of a subject and a second image including an image of an object in a visual line direction of the subject;

deciding, by an arithmetic section, a first mapping for transforming the first image to an environmental map, and a second mapping for transforming the second image to an environmental map;

extracting, by the arithmetic section, a pair of corresponding points by detecting one point in the first image and one point in the second image which corresponds to the one point in the first image;

deriving, by the arithmetic section, a rotational mapping for registering an image of the first image in the environmental map and an image of the second image in the environmental map with each other, based on positions and local feature amounts of the one point in the first image and the one point in the second image, the one point in the first image and the one point in the second image composing the pair of corresponding points; and detecting, by the arithmetic section, a gazing reflection point on the first image by detecting a pose of the eyeball from the first image, and obtaining, by the arithmetic section, as a point gazed by the subject, a point corresponding to the gazing reflection point in the second image, based on the first mapping, the rotational mapping, and the second mapping.

(6) A peripheral visual field estimation method including the steps of:

obtaining, by an arithmetic section, a first image including an image of an eyeball of a subject and a second image including an image of an object in a visual line direction of the subject;

deciding, by the arithmetic section, a first mapping for transforming the first image to an environmental map, and a second mapping for transforming the second image to an environmental map;

extracting, by the arithmetic section, a pair of corresponding points by detecting one point in the first image and one point in the second image which corresponds to the one point in the first image;

deriving, by the arithmetic section, a rotational mapping for registering an image of the first image in the environmental map and an image of the second image in the environmental map with each other, based on positions and local feature amounts of the one point in the first image and the one point in the second image, the one point in the first image and the one point in the second image composing the pair of corresponding points;

identifying, by the arithmetic section, an optical axis of the eyeball from the first image;

identifying, by the arithmetic section, reflection points at which lights arriving from directions having predetermined angles with respect to the optical axis are reflected by a corneal surface; and detecting, by the arithmetic section, reflection points identified from the second image, as a group of points composing a region of a peripheral visual field of the subject, based on the first mapping, the rotational mapping, and the second mapping.

(7) An iris recognition method including the steps of:

obtaining data of a first image including an image of an eyeball of a subject and a second image including an image of an object in a visual line direction of the subject;

storing the data of the first image and the data of the second image;

deciding, by the arithmetic section, a first mapping for transforming the first image to an environmental map, and a second mapping for transforming the second image to an environmental map;

extracting, by the arithmetic section, a pair of corresponding points by detecting one point in the first image and one point in the second image which corresponds to the one point in the first image;

deriving, by the arithmetic section, a rotational mapping for registering an image of the first image in the environmental map and an image of the second image in the environmental map with each other, based on positions and local feature amounts of the one point in the first image and the one point in the second image which compose the pair of corresponding points; and registering, by the arithmetic section, the data of the first image stored in the storage device with the data of the second image stored in the storage device in order to generate data of the first image registered with the second image, based on the first mapping, the rotational mapping, and the second mapping;

generating, by the arithmetic section, an iris image by subtracting the registered first image from the second image; and performing, by the arithmetic section, iris recognition with the iris image.

The present invention is described above in association with the specific embodiments. However, it is further understood by those skilled in the art that many changes, modifications, substitutions, deletions, and applications can be made in the present invention. Therefore, the present invention is not limited to a specific disclosure, but limited only to the attached claims.

The invention claimed is:

1. An image registration device, comprising:
one or more data storage devices; and
a controller coupled to the one or more data storage devices, the controller executing programmed instructions stored in the one or more data storage devices to:
obtain data of a first image comprising a scene in a visual line direction of a subject and data of a second image comprising a reflection of at least a portion of the scene on an eyeball of the subject;
store the data of the first image and the data of the second image in the one or more data storage devices;
decide a first mapping for transforming, based on a first transform function, the first image to a first environmental map comprising a first spherical surface and a second mapping for transforming, based on a second transform function, the second image to a second environmental map comprising a second spherical surface, the second transform function comprising a vector indicating a point in the first image in a path of light incident on a corresponding point in the second image;
extract a pair of corresponding points by detecting a first point in the first image and a second point in the second image which corresponds to the first point in the first image;
derive a rotational mapping between the respective first and second spherical surfaces for registering at least a portion of the first image in the first environmental map and at least a portion of the second image in the second environmental map with each other, based on positions and local feature amounts of the first point in the first image and the second point in the second image which compose the pair of corresponding points, said rotational mapping based at least in part on respective normalized vectors associated with the pair of corresponding points and said respective normalized vectors comprising respective functions for transforming orientation information to the respective first and second environmental maps; and register the data of the first image stored in the one or more data storage devices with the data of the second image stored in the one or more data storage devices in order to generate data of the first image registered with the second image, based on the first mapping, the rotational mapping, and the second mapping.

2. The image registration device according to claim 1, wherein the local feature amounts comprise orientation information.

3. The image registration device according to claim 1, wherein the controller detects a plurality of candidate pairs of corresponding points, each as a candidate of the pair of corresponding points comprising the first point of the first image and the second point of the second image, evaluates a correspondence between corresponding points for each candidate pair, and extracts a candidate pair of the corresponding points which are most highly evaluated among the plurality of candidate pairs detected by the controller, as the pair of corresponding points.

4. The image registration device according to claim 3, wherein the controller evaluates the correspondence between the corresponding points for the candidate pair, by evaluating correspondences of plural secondary pairs of corresponding points composed of pairs of corresponding points extracted from the first image and the second image according to the correspondence between the point of the first image and the point of the second image, the point of the first image and the point of the second image composing the candidate pair of corresponding points.

5. An image registration system, comprising:
a first camera that photographs a first image;
a second camera that photographs a second image; and
the image registration device according to claim 1 that performs image registration for the first image and the second image.

6. An image registration method, comprising:
obtaining, by a controller, data of a first image comprising a scene in a visual line direction of a subject and data of a second image comprising a reflection of at least a portion of the scene on an eyeball of the subject;
storing the data of the first image and the data of the second image in one or more data storage devices;
deciding, by the controller, a first mapping for transforming, based on a first transform function, the first image to a first environmental map comprising a first spherical surface and a second mapping for transforming, based on a second transform function, the second image to a second environmental map comprising a second spherical surface, the second transform function comprising a vector indicating a point in the first image in a path of light incident on a corresponding point in the second image;
extracting, by the controller, a pair of corresponding points, by detecting a first point in the first image and a second point in the second image which corresponds to the first point in the first image;
deriving, by the controller, a rotational mapping between the respective first and second spherical surfaces for registering at least a portion of the first image in the first environmental map and at least a portion of the second image in the second environmental map with each other, based on positions and local feature amounts of the first point in the first image and the second point in the second image, the one point in the first image and the one point in the second image composing the pair of corresponding points, said rotational mapping based at least in part on respective normalized vectors associated with the pair of corresponding points and said respective normalized vectors comprising respective functions for transforming orientation information to the respective first and second environmental maps; and
generating, by the controller, data of the first image registered with the second image by registering the data of the first image stored in the one or more data storage devices with the data of the second image stored in the one or more data storage devices based on the first mapping, the rotational mapping, and the second mapping.

7. A non-transitory recording medium storing an image registration program that is executable by a computer, the image registration program causing the computer to perform the functions of:
obtaining, by a controller, data of a first image comprising a scene in a visual line direction of a subject and data of a second image comprising a reflection of at least a portion of the scene on an eyeball of the subject;
storing the data of the first image and the data of the second image in one or more data storage devices;
deciding, by the controller, a first mapping for transforming, based on a first transform function, the first image to a first environmental map comprising a first spherical surface, and a second mapping for transforming, based on a second transform function, the second image to a second environmental map comprising a second spherical surface, the second transform function comprising a vector indicating a point in the first image in a path of light incident on a corresponding point in the second image;
extracting, by the controller, a pair of corresponding points, by detecting a first point in the first image and a second point in the second image which corresponds to the first point in the first image;
deriving, by the controller, a rotational mapping between the respective first and second spherical surfaces for registering at least a portion of the first image in the first environmental map and at least a portion of the second image in the second environmental map with each other, based on positions and local feature amounts of the first point in the first image and the second point in the second image, the one point in the first image and the one point in the second image composing the pair of corresponding points, said rotational mapping based at least in part on respective normalized vectors associated with the pair of corresponding points and said respective normalized vectors comprising respective functions for transforming orientation information to the respective first and second environmental maps; and
generating, by the controller, data of the first image registered with the second image by registering the data of the first image stored in the one or more data storage devices with the data of the second image stored in the one or more data storage devices based on the first mapping, the rotational mapping, and the second mapping.

* * * * *